(12) United States Patent
Okui et al.

(10) Patent No.: US 6,849,633 B2
(45) Date of Patent: Feb. 1, 2005

(54) PYRAZOLE DERIVATIVE, PRODUCTION PROCESS THEREOF, AND PEST CONTROL AGENT CONTAINING THE SAME AS ACTIVE INGREDIENT

(75) Inventors: Shuko Okui, Yokohama (JP); Nobuo Kyomura, Yokohama (JP); Toshiki Fukuchi, Yokohama (JP); Ken Tanaka, Yokohama (JP); Manabu Katsurada, Yokohama (JP); Kazuya Okano, Ibaraki (JP); Naoko Sumitani, Ibaraki (JP); Akiko Miyauchi, Ibaraki (JP); Akiko Yabe, Ibaraki (JP)

(73) Assignee: Nihon Nohyaku Co., Ltd., Tokyo (JP)

( * ) Notice: Subject to any disclaimer, the term of this patent is extended or adjusted under 35 U.S.C. 154(b) by 143 days.

(21) Appl. No.: 10/028,786

(22) Filed: Dec. 28, 2001

(65) Prior Publication Data

US 2003/0060471 A1 Mar. 27, 2003

Related U.S. Application Data

(63) Continuation of application No. PCT/JP00/04258, filed on Jun. 28, 2000.

(30) Foreign Application Priority Data

Jun. 29, 1999 (JP) ............................................ 11-183162

(51) Int. Cl.$^7$ .................... C07D 401/14; C07D 403/12; A01N 43/60
(52) U.S. Cl. .................. 514/255.05; 544/405; 544/333; 544/238; 546/256; 546/275.4
(58) Field of Search ...................... 544/405; 514/255.05

(56) References Cited

U.S. PATENT DOCUMENTS

| | | | |
|---|---|---|---|
| 5,556,873 A | 9/1996 | Huang et al. | 514/407 |
| 5,580,843 A | 12/1996 | Stetter et al. | 514/341 |
| 5,618,945 A | 4/1997 | Casado et al. | 548/367.4 |
| 5,883,112 A | 3/1999 | Pilato et al. | 514/404 |
| 6,335,357 B1 | 1/2002 | Okui et al. | 514/404 |

FOREIGN PATENT DOCUMENTS

| | | |
|---|---|---|
| EP | 0 234 119 | 9/1987 |
| EP | 0 295 117 | 12/1988 |
| EP | 0 418 016 | 3/1991 |
| EP | 0 511 845 | 11/1992 |
| EP | 0 579 280 | 1/1994 |
| JP | 62-228065 | 10/1987 |
| JP | 63-316771 | 12/1988 |
| JP | 64-47768 | 2/1989 |
| JP | 3-118369 | 5/1991 |
| JP | 10-7509 | 1/1998 |
| WO | WO 98/45274 | 10/1998 |
| WO | WO 01/30760 | 5/2001 |

OTHER PUBLICATIONS

U.S. Appl. No. 10/028,786, Okui et al., filed Dec. 28, 2001.
U.S. Appl. No. 10/355,182, Okui et al., filed Jan. 31, 2003.

Primary Examiner—Mark L Berch
Assistant Examiner—Kahsay Habte
(74) Attorney, Agent, or Firm—Oblon, Spivak, McClelland, Maier & Neustadt, P.C.

(57) ABSTRACT

The invention provides a novel pest control agent having a high systemic activity and a high safety with reduced adverse influences on the environment neighboring the place to which the agent is applied, and a process for producing the same.

Namely, the present invention relates to a novel 1-aryl-3-cyano-5-heteroarylalkylaminopyrazole derivative represented by the following general formula (1) and a process for producing the same, and a pest control agent containing the same as an active ingredient.

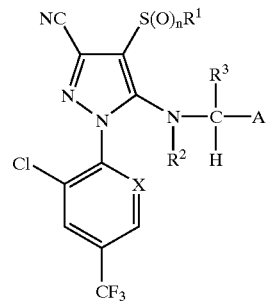

(1)

A:

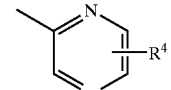

A-1

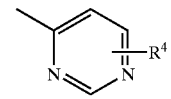

A-2

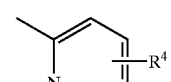

A-3

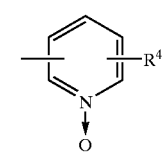

A-4

(wherein X represents N or C-halogen, R$^1$ represents an alkyl group, an alkenyl group, an alkynyl group, or a haloalkyl group, R$^2$ represents hydrogen atom, an alkyl group, or an acyl group, R$^3$ represents hydrogen atom or an alkyl group, A represents any one of the groups represented by A-1 to A-4, R$^4$ represents hydrogen atom, an alkyl group, a halogen atom, and n represents 0, 1, or 2, provided that R$^1$ is a haloalkyl group except a perhaloalkyl group when A is A-1 and n is 0, and that n is not 0 when A is A-4.).

32 Claims, No Drawings

PYRAZOLE DERIVATIVE, PRODUCTION PROCESS THEREOF, AND PEST CONTROL AGENT CONTAINING THE SAME AS ACTIVE INGREDIENT

This application is a continuation of PCT/JP00/04258 filed Jun. 28, 2000.

TECHNICAL FIELD

The present invention relates to a novel 1-aryl-3-cyano-5-heteroarylalkylaminopyrazole derivative and a pest control agent containing the same as an active ingredient.

BACKGROUND OF THE INVENTION

In the agricultural and horticultural field, a wide variety of insecticides have been hitherto developed and put into practical use for the purpose of controlling various pest insects.

Examples of pyrazole compounds known to have insecticidal activity include 3-cyano-1-phenylpyrazole derivatives having an optionally substituted amino group at the 5-position disclosed in Japanese Patent Laid-open Nos. 228065/1987, 316771/1988 and 118369/1991, substituted 1-aryl-3-cyano-5-(het)arylmethylideneiminopyrazole derivatives disclosed in an Japanese Patent Laid-open No. 148240/1993, and substituted 1-aryl-5-(het)arylmethylaminopyrazole derivatives disclosed in Japanese Patent Laid-Open No. 47768/1989.

However, the compounds described in the above literatures are not necessarily satisfactory in all of insecticidal effect, insecticidal spectrum, safety, and the like, and thus the development of novel compounds overcoming these problems has been desired. As a result, novel 1-aryl-3-cyano-5-heteroarylalkylaminopyrazole derivatives are disclosed as compounds exhibiting a high safety in WO98/45274.

However, no specific compounds wherein the hetero ring is pyrazine ring, pyridazine ring, or pyrimidine ring are disclosed in the application.

The compounds disclosed in WO98/45274 and the like are excellent in insecticidal activity and have a reduced toxicity as compared with known compounds. In recent years, the safety to organisms other than target pest insects and the environment has been increasingly demanded and, hereafter, measures for environmental protection will be strongly taken. Therefore, in order to develop pesticides satisfying more strict regulation, it has been an important problem to find out compounds exhibiting a higher safety.

In addition, in view of efficient application of an agent for pest control and application for soil treatment especially effective for controlling pest organisms such as fluid-sucking pests, systemic activity is an important factor, so that it has been desired to find out novel compounds having both of these properties.

DISCLOSURE OF THE INVENTION

As a result of the extensive studies for solving the above problems, the present inventors have found that a compound wherein a specific nitrogen-containing six-membered heterocycle is introduced into an amino group at 5-position of the pyrazole ring in a pyrazole compound, a 1-aryl-3-cyano-5-heteroarylalkylaminopyrazole derivative exhibits selectively a high systemic activity and has a low toxicity to the environment as shown by toxicity to fishes.

Moreover, they have found that a higher effect can be attained by optimization of the combination of the heteroaryl group and the substituent at 4-position of the pyrazole ring, and have accomplished the invention.

Namely, the gist of the present invention lies in a 1-aryl-3-cyano-5-heteroarylalkylaminopyrazole derivative represented by the following general formula (1):

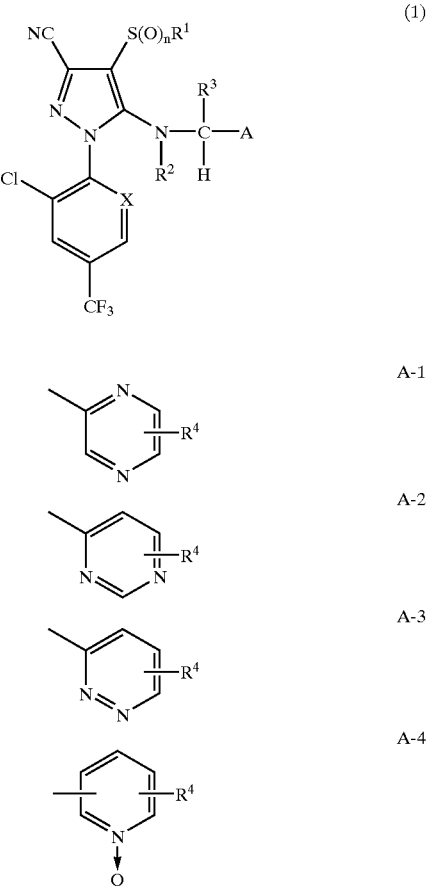

(wherein X represents N or C-halogen, $R^1$ represents an alkyl group, an alkenyl group, an alkynyl group, or a haloalkyl group, $R^2$ represents hydrogen atom, an alkyl group, or an acyl group, $R^3$ represents hydrogen atom or an alkyl group, A represents any one of the groups represented by A-1 to A-4, $R^4$ represents hydrogen atom, an alkyl group, a halogen atom, and n represents 0, 1, or 2, provided that $R^1$ is a haloalkyl group except a perhaloalkyl group when A is A-1 and n is 0, and that n is not 0 when A is A-4), and a pest control agent containing the same as an active ingredient.

The following will explain the invention in detail.

Compounds of the Invention

In the invention, the substituent $R^1$ in the compounds represented by the above general formula (1) represents a linear or branched alkyl group such as methyl group, ethyl group, n-propyl group, isopropyl group, n-butyl group, isobutyl group, sec-butyl group, or t-butyl group; a linear or branched alkenyl group such as vinyl group, allyl group, methallyl group, or 2-butenyl group; a linear or branched alkynyl group such as ethynyl group or propargyl group; or a linear or branched haloalkyl group such as fluoromethyl group, difluoromethyl group, trifluoromethyl group, 2-fluoroethyl group, 2-chloroethyl group, 2,2,2-trifluoroethyl group, 2,2,2-trichloroethyl group, 3-chloropropyl group, 3-bromopropyl group, 3,3,3- trifluoropropyl group, 2,2,3,3-tetrafluoropropyl group, 2,2,3,3,3-pentafluoropropyl group, 2,2-dichloro-3,3,3-trifluoropropyl group, 2,2-dichloro-3,3,3-trifluoropropyl group, 1,3-difluoro-2-propyl group, 1,1,1,3,3,3-hexafluoro-2-propyl group, 3,3,3-trichloropropyl group, 4-chlorobutyl group, 4,4,4-trifluorobutyl group, or 3,3,4,4,4-pentafluorobutyl group. Preferred of them is a $C_1$–$C_4$ alkyl group, a $C_1$–$C_4$ alkenyl group, a $C_1$–$C_4$ alkynyl group, or a $C_1$–$C_4$ haloalkyl group. Particularly preferred is a $C_1$–$C_4$ alkyl group or a $C_1$–$C_4$ haloalkyl group. Among them, preferred is a $C_1$–$C_2$ alkyl group or a $C_1$–$C_2$ haloalkyl group, and particularly preferred is a $C_1$–$C_2$ haloalkyl group such as fluoromethyl group, difluoromethyl group, trifluoromethyl group, 2-fluoroethyl group, or 2-chloroethyl group.

$R^2$ represents hydrogen atom; a linear or branched alkyl group such as methyl group, ethyl group, n-propyl group, isopropyl group, n-butyl group, isobutyl group, sec-butyl group, or t-butyl group; or a linear or branched acyl group such as methylcarbonyl group, ethylcarbonyl group, n-propylcarbonyl group, isopropylcarbonyl group, n-butylcarbonyl group, isobutylcarbonyl group, sec-butylcarbonyl group, or t-butylcarbonyl group. Preferred of them is a $C_1$–$C_4$ alkyl group or a $C_1$–$C_4$ acyl group. Particularly preferred of $R^2$ is hydrogen atom.

$R^3$ represents hydrogen atom; or a linear or branched alkyl group such as methyl group, ethyl group, n-propyl group, isopropyl group, n-butyl group, isobutyl group, sec-butyl group, or t-butyl group. Preferred of the above alkyl group is a $C_1$–$C_4$ alkyl group. Particularly preferred of $R^3$ is hydrogen atom.

A is any one of the groups represented by A-1 to A-4, and preferred of them is A-1. The invention is characterized in that a nitrogen-containing six-membered heterocycle having the above specific structure is selected and the ring is bonded to the amino group at 5-position of the pyrazole ring via methylene group.

$R^4$ represents hydrogen atom; a linear or branched alkyl group such as methyl group, ethyl group, n-propyl group, isopropyl group, n-butyl group, isobutyl group, sec-butyl group, or t-butyl group; or a halogen atom such as chlorine atom, fluorine atom, or bromine atom. With regard to the alkyl group, preferred is a $C_1$–$C_4$ alkyl group. Particularly preferred of $R^4$ is hydrogen atom.

X is N or C-halogen atom. Among them, preferred is C-halogen atom, and particularly preferred is C-chlorine atom.

n is any of 0, 1, or 2, and preferably n is 0 or 1, provided that n is not 0 when A is A-4.

Moreover, when A is A-1 and n is 0, $R^1$ is a haloalkyl group except a perhaloalkyl group. Among them, preferred is a $C_1$–$C_4$ haloalkyl group, particularly preferred is a $C_1$–$C_2$ haloalkyl group, most preferred is a $C_1$ fluorinated alkyl group such as fluoromethyl group or difluoromethyl group.

As the compounds of the above general formula (1), the compounds derived from the combinations of each preferable substituent in the above explanation of the substituents are more preferable compounds.

Among them, a preferred compound as a combination of the substituents is the compound wherein $R^2$, $R^3$, and $R^4$ are each hydrogen atom, X is C—Cl group, and A is A-1.

In the case that n is other than 0, $R^1$ is preferably an alkyl group or a haloalkyl group, more preferably a $C_1$–$C_4$ alkyl group or a $C_1$–$C_4$ haloalkyl group, and particularly preferably a $C_1$–$C_2$ haloalkyl group. Moreover, in the case that n is 0, $R^1$ is a haloalkyl group other than a perhaloalkyl group, preferably a $C_1$–$C_4$ haloalkyl group, and particularly preferably a $C_1$–$C_2$ fluorinated alkyl group.

Among them, the compounds wherein $R^1$ is a $C_1$ haloalkyl group, i.e., fluoromethyl group, difluoromethyl group, or trifluoromethyl group (excluding trifluoromethyl group when n is 0) is preferable because they have a high insecticidal activity and a low toxicity to fishes when they are used as pest control agents, especially as active ingredients for insecticides.

Among the combinations of the above substituents, the most preferable compounds are 1-(2,6-dichloro-4-trifluoromethylphenyl)-4-fluoromethylthio-5-(pyrazin-2-ylmethylamino)pyrazole-3-carbonitrile and 1-(2,6-dichloro-4-trifluoromethylphenyl)-4-trifluoromethylsulfinyl-5-(pyrazin-2-ylmethylamino)pyrazole-3-carbonitrile.

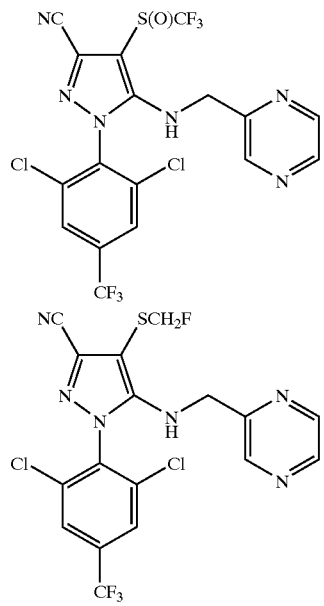

Process for Producing the Compounds of the Invention

With regard to the process for producing the compounds of the invention represented by the above general formula (1), the compounds can be produced by forming the pyrazole ring and then incorporating or changing substituent(s), if necessary.

Known processes include processes described in Japanese Patent Laid-Open Nos. 316771/1988, 148240/1993, 47768/1989, and 47768/1989. As a process for production using these processes, the process shown in Reaction Scheme 1 is exemplified.

Reaction Scheme 1

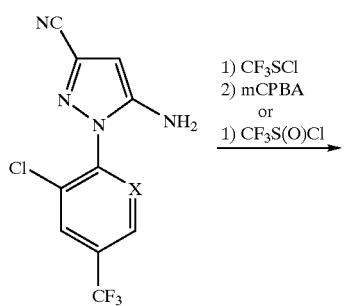

1) $CF_3SCl$
2) mCPBA
or
1) $CF_3S(O)Cl$

-continued

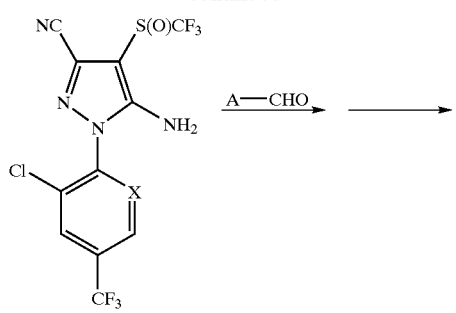

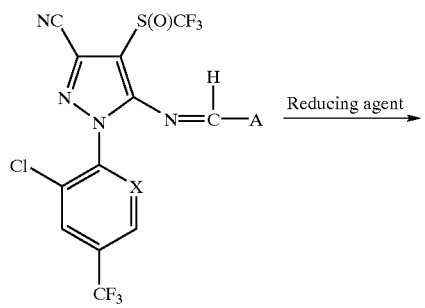

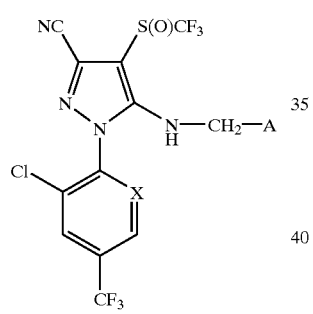

However, this process has a defect that an expensive fluorine-containing reagent is used at the early stage of the steps. Alternatively, the processes shown in Reaction Schemes 2 and 3 are possible but similar problems such as availability of starting materials arise.

Reaction Scheme 2

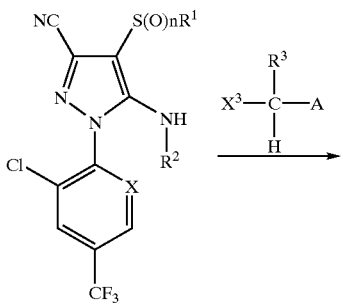

-continued

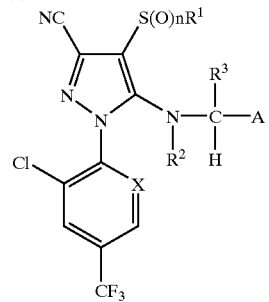

Reaction Scheme 3

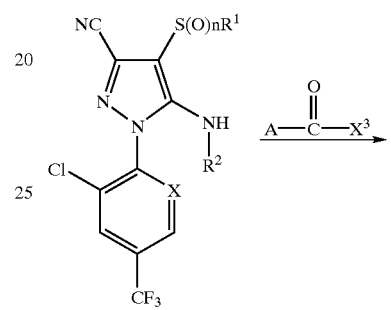

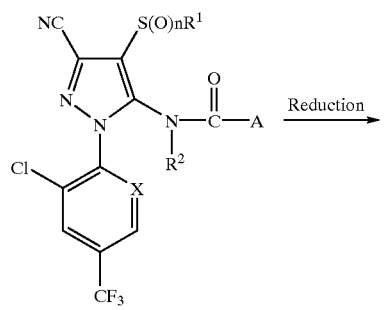

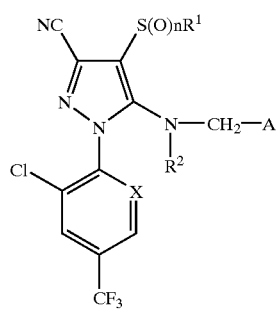

Moreover, WO98/45274 discloses that a pyrazole derivative having 4-pyridylmethylamino group at the 5-position can be obtained by treating the amino group present at the 5-position of a pyrazole derivative with pyridyl-4-aldehyde to form an imine and then reducing the imine (Reaction Scheme 4).

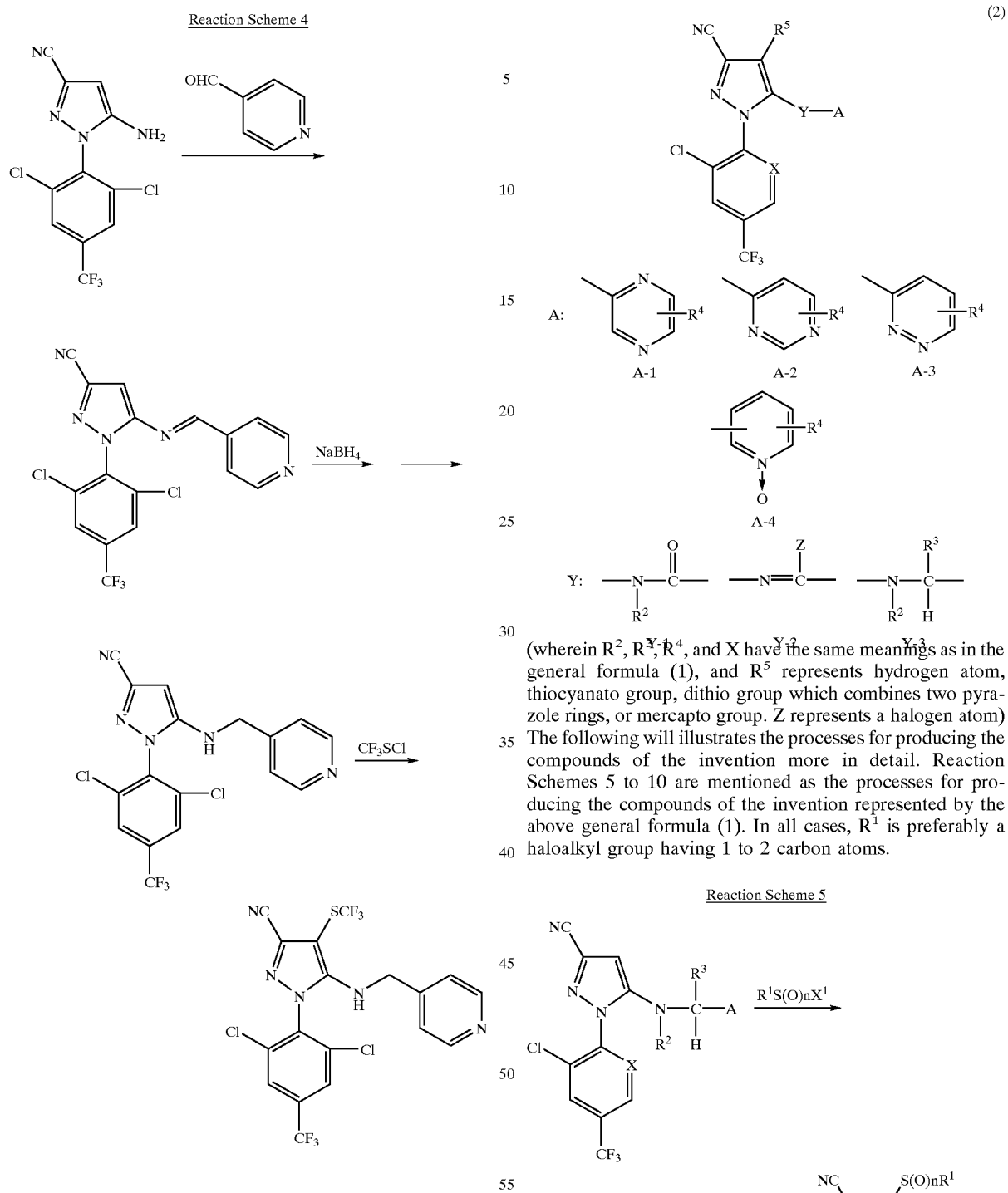

It is also possible to synthesize the compounds of the invention according to the process shown in above Reaction Scheme (4), but as a result of further studies, the present inventors have found that the processes shown in following Reaction Schemes 5 to 10 are more efficient as the processes for producing the pyrazole derivatives represented by the general formula (1) of the present patent application. The following general formula (2) are intermediates for the production of the compounds of the general formula (1) in accordance with the above processes.

(wherein $R^2$, $R^3$, $R^4$, and X have the same meanings as in the general formula (1), and $R^5$ represents hydrogen atom, thiocyanato group, dithio group which combines two pyrazole rings, or mercapto group. Z represents a halogen atom)

The following will illustrates the processes for producing the compounds of the invention more in detail. Reaction Schemes 5 to 10 are mentioned as the processes for producing the compounds of the invention represented by the above general formula (1). In all cases, $R^1$ is preferably a haloalkyl group having 1 to 2 carbon atoms.

Reaction Scheme 6

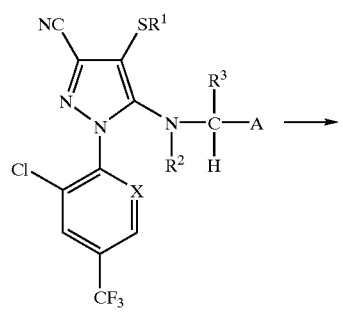

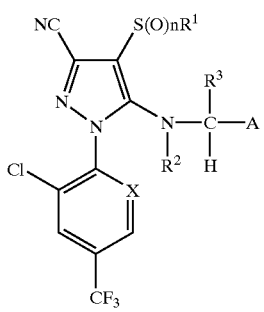

Reaction Scheme 7

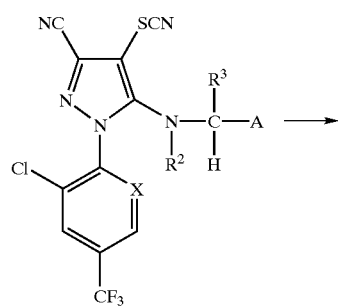

Reaction Scheme 8

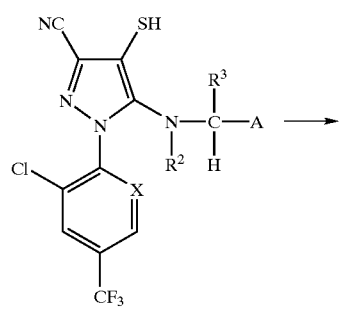

-continued

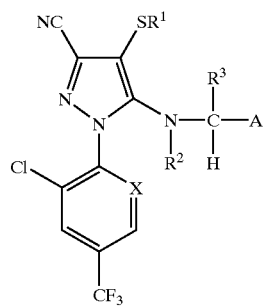

Reaction Scheme 9

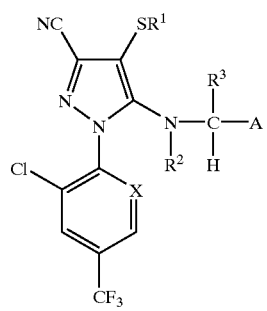

Reaction Scheme 5 represents a process for producing a pyrazole derivative of the general formula (1), which comprises treating a pyrazole derivative of the general formula (2) wherein $R^5$ is hydrogen atom and Y is Y-3, with $R^1S(O)_nX^1$ wherein $R^1$ and n have the same meaning as in the general formula (1) and $X^1$ is chlorine atom or bromine atom. $X^1$ is preferably chlorine atom. When n is 0, preferred example of the employed reagent, $R^1S(O)_nX^1$ is trifluoromethylsulfenyl chloride ($CF_3SCl$) and in this case, the resulting compound is a pyrazole derivative having trifluoromethylsulfenyl group at the 4-position. When n is 1, preferred example of the employed reagent, $R^1S(O)_nX^1$ is trifluoromethylsulfinyl chloride ($CF_3SOCl$) and in this case, the resulting compound is a pyrazole derivative having trifluoromethylsulfinyl group at the 4-position.

The following will illustrate this reaction using trifluoromethylsulfenyl chloride and trifluoromethylsulfinyl chloride as representative examples, but the reaction can be carried out in a similar manner in the case that other reagents are used.

When trifluoromethylsulfinyl chloride is used, trifluoromethylsulfinyl chloride isolated beforehand may be used or it may be generated in situ from sodium salt or potassium salt of trifluoromethylsulfinic acid and thionyl chloride. Also, a pyrazole wherein the 4-position is sulfenylated in the reaction with the salt of trifluoromethylsulfinic acid depending on the reaction conditions.

In the reaction, $R_1S(O)_nX_1$ is used in an amount of 0.5 to 10.0 molar equivalents, preferably 0.8 to 5 molar equivalents to the compound represented by the general formula (2) (wherein $R^5$ is hydrogen atom) and the reaction is carried out at 0° C. to 150° C., preferably 0° C. to 100° C. The solvent for use in the reaction includes aromatic hydrocarbons such as benzene, toluene, or xylene; ketones such as acetone or methyl ethyl ketone; halogenated hydrocarbons such as chloroform or methylene chloride; polar solvents such as tetrahydrofuran or N,N-dimethylformamide. Particularly, toluene and dichloromethane are preferred.

The reaction may be carried out in the absence of a base when trifluoromethylsulfenyl chloride is used but is preferably carried out in the presence of a base, and an amine such as pyridine or triethylamine is used. When trifluoromethylsulfinyl chloride or a salt of trifluoromethylsulfinic acid is used, an amine such as dimethylamine, pyridine, or triethylamine or an inorganic base such as an alkali metal carbonate is used in combination with an acid such as sulfuric acid, hydrochloric acid, or toluenesulfonic acid. Preferred is a combination of dimethylamine and toluenesulfonic acid. These may be added separately but preferably added as the salt of dimethylamine and toluenesulfonic acid (dimethylamine tosylate).

Reaction Scheme 6 represents a process for producing a pyrazole derivative of the general formula (1) wherein n is 1 or 2, which comprises oxidizing the sulfur atom of a pyrazole derivative of the general formula (1) wherein n is 0. Examples of the methods for oxidation include chemical oxidation using an oxidizing agent and biological oxidation using an enzyme or a fungus, but chemical oxidation is generally employed. In chemical oxidation, an oxidizing agent is added in an amount of 0.2 to 5.0 molar equivalents, preferably 0.25 to 2.0 molar equivalents to the compound of the general formula (2) in the absence or presence of a solvent, and the reaction is carried out at −20 to 150° C., preferably 0 to 20° C.

The oxidizing agent for use in the reaction includes hydrogen peroxide, Oxone, m-chloroperbenzoic acid, peracetic acid, sodium periodate, ruthenium tetroxide, ozone, t-butyl hydroperoxide, nitric acid, and the like. Preferred is hydrogen peroxide.

The solvent for use in the reaction may be an organic solvent generally used for oxidation, and use is made of a hydrocarbon solvent such as toluene or hexane or a halogenated hydrocarbon solvent such as dichloromethane or chloroform.

Particularly in the invention, the reaction is suitably carried out in the presence of an acid. The acid to be used may be exemplified by a protonic acid and a Lewis acid but preferred is a protonic acid. Examples of the protonic acid include inorganic acids such as sulfuric acid, hydrochloric acid, nitric acid, and phosphoric acid, diluted sulfuric acid, and organic acids such as acetic acid, formic acid, and trifluoroacetic acid. Preferred is an inorganic acid and more preferred is sulfuric acid. When sulfuric acid is used, diluted sulfuric acid having a concentration of 60 to 90%, preferably 75 to 85% is used. Each of these acids may be used as a mixture with an organic solvent, but preferably, the acid itself is used as a solvent.

Preferred combination of an oxidizing agent and a solvent is the combination of hydrogen peroxide and diluted sulfuric acid.

In the reaction, a catalyst for accelerating the oxidation may be added, if necessary. As the catalyst, use can be generally made of a catalyst for accelerating the oxidation of a sulfide. Preferred is a ruthenium compound, a tungsten compound, a vanadium compound, a molybdenum compound, titanium compound, or the like, and more preferred is a ruthenium compound. Examples of the ruthenium compound may include ruthenium trichloride and ruthenium oxide. The amount of the catalyst to be used is, for example, from 0.01 to 100 mol %, preferably 0.1 to 20 mol % relative to the starting sulfide.

The reaction is carried out at a temperature of −30 to 120° C., preferably −10° C. to room temperature for 1 to 48 hours, preferably 1 to 6 hours.

Reaction Scheme 7 represents a process for producing a pyrazole derivative of the general formula (1) wherein n is 0, which comprises treating a pyrazole derivative of the general formula (2) wherein $R^5$ is thiocyanato group and Y is Y-3, with $R^1$—$X^2$ wherein $R^1$ has the same meaning as in the general formula (1) and $X^2$ represents a halogen atom or trimethylsilyl group.

Examples of the reagent for use in the reaction include trifluoromethyl bromide, trifluoromethyl iodide, and trifluoromethyltrimethylsilane. Preferred is trifluoromethyltrimethylsilane.

Examples of the solvent for use in the reaction include ether solvents such as tetrahydrofuran, diethyl ether, and dimethoxyethane; hydrocarbon solvents such as toluene and xylene; and halogenated hydrocarbon solvents such as dichloromethane and chloroform. Preferred is tetrahydrofuran.

The reaction is preferably carried out in the presence of a fluorine compound and preferred is tetrabutylammonium fluoride or potassium fluoride.

In the reaction, the reagent $R^1$—$X^2$ is used in an amount of 0.5 to 10.0 molar equivalents, preferably 0.8 to 5 molar equivalents to the compound represented by the general formula (2) wherein $R^5$ is hydrogen atom. The reaction is carried out at a temperature of −20 to 120° C., preferably 0° C. to room temperature for 1 to 24 hours, preferably 1 to 4 hours.

Reaction Scheme 8 represents a process for producing a pyrazole derivative of the general formula (1) wherein n is 0, which comprises treating a pyrazole derivative of the general formula (2) wherein $R^5$ is mercapto group and Y is Y-3, with $R^1$—$X^3$ wherein $R^1$ has the same meaning as in the general formula (1) and $X^3$ represents a halogen atom.

Examples of the reagent to be used include trifluoromethyl bromide and trifluoromethyl iodide.

Examples of the solvent include polar solvents such as DMF and DMSO; hydrocarbon solvents such as toluene and hexane; halogenated hydrocarbon solvents such as dichloromethane and chloroform; basic solvents such as triethylamine and liquid ammonia. Preferred is a polar solvent such as DMF.

The reaction is preferably carried out under trifluoromethyl radical-forming conditions, and specific examples include irradiation with light and use of a radical initiator, a redox agent, or an electron transfer agent such as methylviologen.

The reaction is carried out at a temperature of −20 to 120° C., preferably 0° C. to room temperature for 1 to 24 hours, preferably 1 to 4 hours.

Reaction Scheme 9 represents a process for producing a pyrazole derivative of the general formula (1) wherein n is 0 and $R^3$ is hydrogen atom, which comprises treating a pyrazole derivative of the general formula (2) wherein $R^5$ is dithio group combining two pyrazole rings and Y is Y-3, with $R^1$—$X^4$ wherein $R^1$ has the same meaning as in the general formula (1) and $X^4$ represents a halogen atom or $SO_2M$ (M represents an alkali metal).

Examples of the reagent to be used include trifluoromethyl bromide, trifluoromethyl iodide, and a salt of trifluoromethylsulfinic acid.

Examples of the solvent include polar solvents such as DMF and DMSO; hydrocarbon solvents such as toluene and hexane; halogenated hydrocarbon solvents such as dichloromethane and chloroform. Preferred is a polar solvent such as DMF.

The reaction is preferably carried out under trifluoromethyl radical-forming conditions, and specific examples include irradiation with light and use of a radical initiator, a redox agent, or an electron transfer agent such as methylviologen.

In the case of trifluoromethyl bromide and trifluoromethyl iodide, an agent for radical anion formation of sulfur dioxide is preferably used in combination. Examples of the agent for radical anion formation of sulfur dioxide include sodium dithionate ($Na_2SO_4$), sodium hydroxymethanesulfinate (Rongalit, $NaO_2SCH_2OH$), zinc hydroxymethanesulfinate, a mixture of sulfur dioxide and zinc, and a mixture of sulfur dioxide and formic acid or a salt thereof.

The reaction is carried out at a temperature of −20 to 120° C., preferably 0° C. to room temperature for 1 to 24 hours, preferably 1 to 4 hours.

Reaction Scheme 10

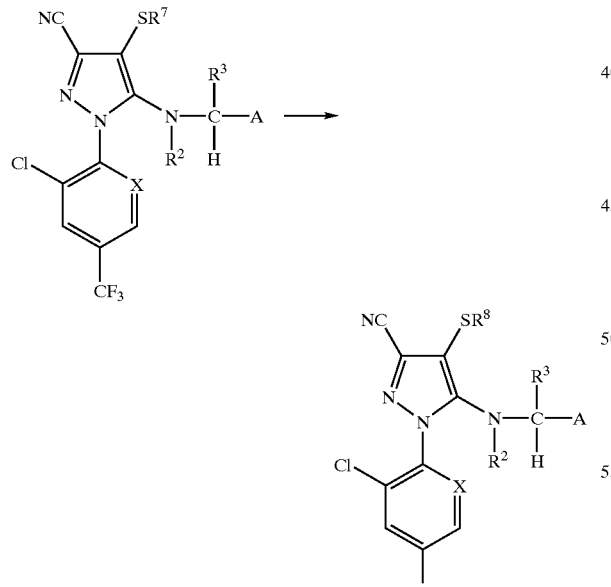

Reaction Scheme 10 represents a process for producing a pyrazole derivative of the general formula (1) wherein $R^1$ is an alkyl group having one or more fluorine atoms, which comprises treating a pyrazole derivative of the general formula (1) wherein $R^1$ is an alkyl group containing one or more chlorine atoms or bromine atoms, with a fluorinating agent selected from the group consisting of hydrogen fluoride, a mixture of hydrogen fluoride and an amine, and a metal fluoride.

The reagent to be used includes hydrogen fluoride, a mixture of hydrogen fluoride and an amine, and a metal fluoride such as potassium fluoride, sodium fluoride, or cobalt fluoride. Preferred is a mixture of hydrogen fluoride and an amine. A solvent generally used for the fluorination through halogen exchange can be employed as the solvent, and preferred is a polar solvent such as DMF. $R^7$ in the starting material is preferably trichloromethyl group, and trifluorometyl group may be mentioned as the $R^8$.

The processes for producing the pyrazole derivatives represented by the general formula (1) are illustrated in the above, and preferred are the processes shown in Reaction Schemes 5 and 6.

The following will illustrate the processes for producing the pyrazole derivatives represented by the general formula (2). When Y is Y-3, the pyrazole derivatives represented by the general formula (2) can be produced according to the processes shown in Reaction Schemes 11 and 12 starting with the compounds represented by the general formula (3) and the general formula (4).

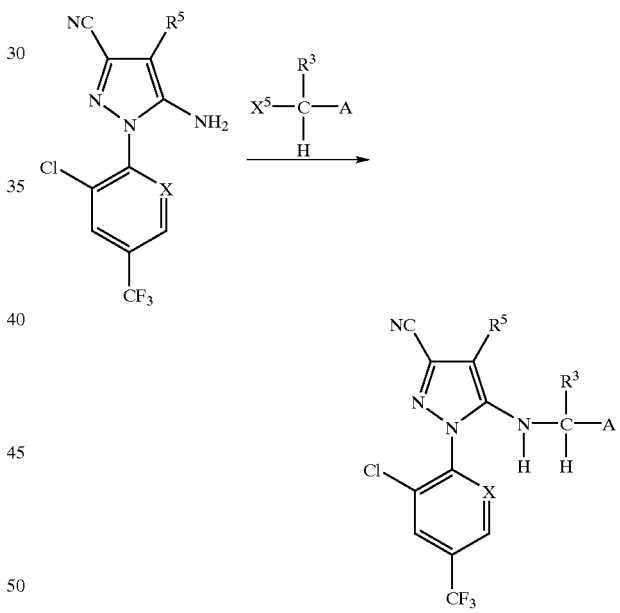

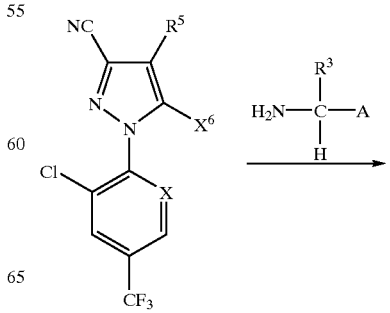

-continued

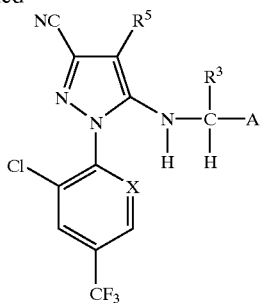

The chlorinating agent for use in the haloimidation includes phosphorus pentachloride, phosphorus oxy chloride, thionyl chloride, and the like.

The solvent for use in the reaction includes non-polar solvents such as benzene, toluene, and xylene; halogenated solvent such as carbon tetrachloride, chloroform, and dichloromethane; and ether solvents such as dimethoxyethane and tetrahydrofuran.

The reaction is carried out at a temperature of 0 to 200° C., preferably room temperature to 150° C. for 1 to 24 hours, preferably 1 to 4 hours.

The compounds represented by the general formula (1) can be produced by combining the above-described pro- Reaction Scheme 13

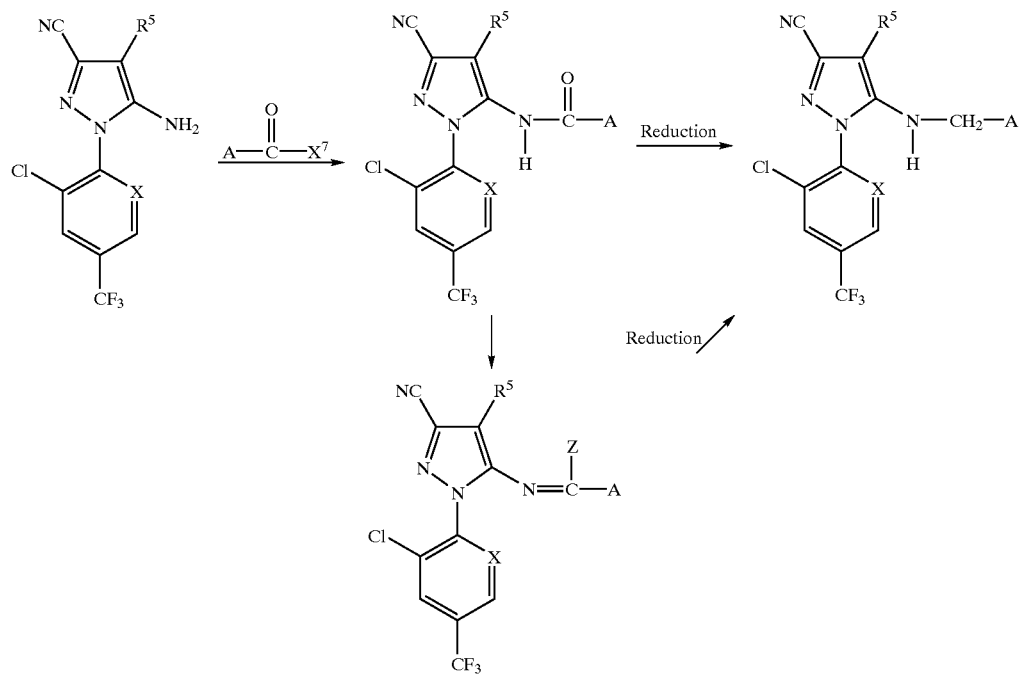

Moreover, as shown in the above Reaction Scheme 13, there may be mentioned a process wherein a starting material, a compound of the general formula (3), is first reacted with A—C(=O)—$X^7$ to form an amide compound (a compound wherein Y is Y-1 in the general formula (2)), which is then reduced to form a compound wherein Y is Y-3 in the general formula (2). Also, another process can be mentioned wherein an amide compound (a compound wherein Y is Y-1 in the general formula (2)) is converted into a haloimidate compound (a compound wherein Y is Y-2 in the general formula (2)), which is then reduced to form a pyrazole derivative wherein Y is Y-3 in the general formula (2).

The reducing agent for use in the reduction includes boran-THF complex, sodium borohydride, sodium cyanoborohydride, lithium borohydride, lithium aluminum hydride, or the like.

The solvent for use in the reaction includes polar solvents, for example, ethers such as diethyl ether, dioxane, or tetrahydrofuran; alcohols such as methanol, ethanol, or propanol; and the like.

The reaction is carried out at a temperature of –20 to 120° C., preferably 0° C. to room temperature for 1 to 24 hours, preferably 1 to 4 hours.

cesses. The process for producing 1-(2,6-dichloro-4-trifluoromethylphenyl)-4-trifluoromethylsulfinyl-5-(pyrazin-2-ylmethylamino)pyrazole-3-carbonitrile is shown in following Reaction Scheme 14 as a typical production process.

Reaction Scheme 14

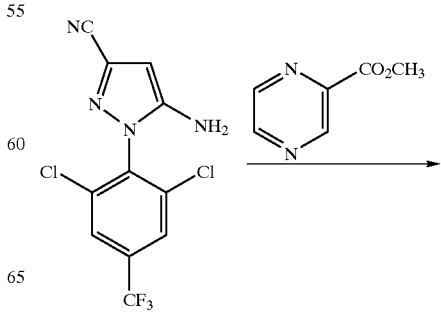

-continued

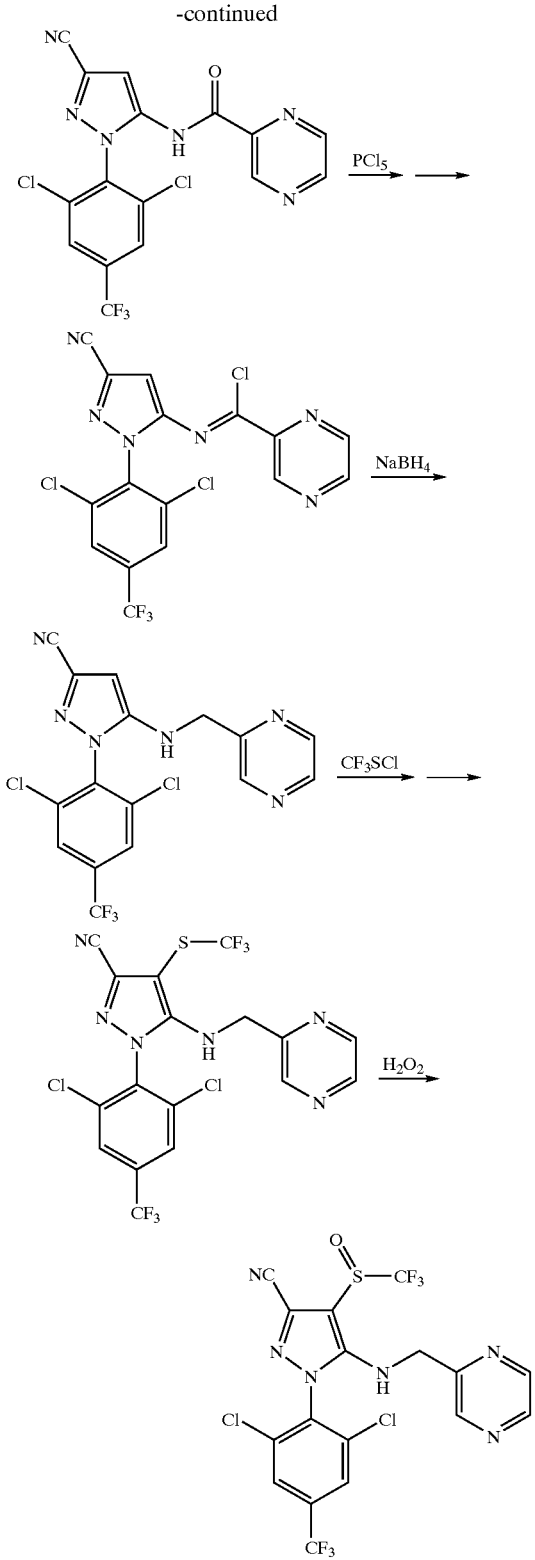

Use of the Compounds of the Invention

The pest control agent containing the compound of the invention as an active ingredient has an effect of controlling pests such as pest insects and mites, and is effective for repelling, expelling, and controlling pests in wide range of scenes at agriculture, forestry, stock raising, fisheries, and preservation of the products of these industries, and public health, for example.

In particular, the compound of the invention exhibits excellent effects as insecticides and acaricides for use at repelling, expelling, and controlling pests in agriculture, forestry, and the like, specifically pests damaging agricultural crops at their raising, harvested crops, trees, plants for appreciation, and the like, and pests in the public health scene.

The following will illustrate specific application scenes, target pests, application methods, and the like, but the invention is not limited to the following descriptions. Furthermore, target pests are not limited to the pests specifically mentioned, and the pests include imagoes, larvae, eggs, and the like thereof.

(A) Agricultural and Forestry Scenes

The pest control agent containing the compound of the invention as an active ingredient is effective for repelling and controlling pests such as arthropods, mollusks, nematoda, various fungi, and the like, which damage agricultural crops, such as food crops (e.g., rice plant, oats, maize, potato, sweet potato, beans), vegetables (e.g., brassicaceous crops, cucurbitaceous fruits, eggplant, tomato, onions), fruit trees (e.g., citrus fruits, apple, grapes, peach), industrial crops (e.g., tobacco, tea, sugar beet, sugar cane, cotton, olive), crops for pasture and feed (solgums, grass pastures, leguminous pastures), plants for appreciation (herbage, flowers and ornamental plants, garden trees) at the raising of these crops. Furthermore, the compound of the invention is also effective for repelling and controlling pests at the storage of harvest products from the above crops, for example, food grains, fruits, nuts, spices, and tobacco, and products resulting from subjecting them to a treatment such as drying or pulverization. Moreover, the compound is also effective for protecting standing trees, fallen trees, processed timber, stored woods from the damage by pests such as termites or beetles.

As specific pests belonging to Arthropoda, Mollusca, and Nematoda, the following may be mentioned, for example. Examples of Arthropoda Insecta include the following.

Examples of Lepidoptera include Noctuidae such as *Leucania unipuncta, Heliothis assulata, Barathra brassicae*, and *Plusia peponis*; Putellidae such as *Plutella maculipennis*; Tortricidae such as *Homona magnanima* and *Grapholita molesta*; Psychidae such as *Canephora asiatica*; Lyonetiidae such as *Lyonetia clerkella*; Lithocolletidae such as *Lithocolletis ringoniella*; Acrolepiidae such as *Acrolepia alliella*; Aegeriidae such as *Aegeria molybdoceps*; Heliodimidae such as *Kakivoria flavofasciata*; Gelechiidae such as *Pectinophora gossypiella*; Carposimidae such as *Carposina nipponensis*; Heterogeneidae such as *Cnidocampa flavescens*; Pyralidae such as *Cnaphalocrocis medinalis, Chilo suppressalis*, and *Natarcha derogate*; Hesperiidae such as *Parnara guttata*; Papilionidae such as *Papilio machaon*; Pieridae such as *Pieris rapae*; Lycaenidae such as *Lampides boeticus*; Geometridae such as *Ascotis selenaria cretacea*; Sphingidae such as *Herse convolvuli*; Notodontidae such as *Phalera flavescens*; Lymantriidae such as *Euproctis subflava*; and Arctiidae such as *Hyphantria cunea*.

Examples of Coleoptera include Scarabaeldae such as *Anomala cuprea, Oxycetonia jucunda*, and *Popillia japonica*; Buprestidae such as *Agrilus auriventris*; Elateridae such as *Melanotus legatus*; Coccinellidae such as *Epilachna vigintioctopunctata*; Cerambycidae such as *Anoplophora malasiaca* and *Xylotrechus pyrrhoderus*; Chrysomelidae such as *Aulacophora femoralis, Phyllotreta striolata*, and *Donacia provostii*; Attelabidae such as *Phyn-* chites heros; Brenthidae such as *Cylas formicarius*; and Curculionidae such as *Curculio sikkimensis* and *Echinocnemus squameus*.

Examples of Hemiptera include Pentatomidae such as *Plautia stali* and *Halyomorpha halys*; Urostylidae such as *Urochela luteovaria*; Coreidae such as *Cletus punctiger*; Alydidae such as *Leptocorisa chinensis*; Pyrrhocoridae such as *Dysdercus cingulatus*; Tingidae such as *Stephanitis nashi*; Miridae such as *Deraeocoris amplus*; Cicadidae such as *Platypleura kaempferi*; Aphrophoridae such as *Dophoara vitis*; Tettigellidae such as *Oniella leucocephala*; Cicadellidae such as *Arboridia apicalis* and *Empoasca onukii*; Deltocephalidae such as *Nephotettix cincticeps*; Delphacidae such as *Laodelphax striatellus* and *Nilaparvata lugens*; Flatidae such as *Geisha distinctissima*; Psylloidae such as *Psylla pyrisuga*; Aleyrodidae such as *Trialeurodes vaporariorum* and *Bemisia argentifolii*; Phylloxeridae such as *Moritziella costaneivora*; Pemphigidae such as *Eriosoma lanigera*; Aphididae such as *Aphis gossypii; Myzus persicae*, and *Rhopalosiphum rufiabdominalis*; Margarodidae such as *Icerya purchasi*; Pseudococcidae such as *Planococcus citri*; Coccidae such as *Ceroplastes rubens*; and Diaspididae such as *Quadraspidiotus perniciosus* and *Pseudaulacaspis pentagana*.

Examples of Thysanoptera include Thripidae such as *Frankliniella occidentalis, Scirtothrips dorsalis*, and *Thrips palmi*; and Phlaeothripidae such as *Ponticulothrips diospyrosi* and *Haplothrips aculeatus*.

Examples of Hymenoptera include Tenthredimidae such as *Athalia japonica*; Argidae such as *Arge mali*; Cynipidae such as *Dryocosmus kuriphilus*; and Megachilidae such as *Megachile nipponica nipponica*.

Examples of Dioptera include Cecidomyiidae such as Asphondylia sp.; Tephiridae such as *Zeugodacus cucurbitae*; Ephydridae such as *Hydrellia griseola*; Drosophilidae such as *Drosophila suzukii*; Agromyzidae such as *Chromatomyia horticola* and *Liziomyza trifolii*; and Anthomyiidae such as *Hylemya antiqua*.

Examples of Orthoptera include Tettigoniidae such as *Homorocoryphus nitidulus*; Gxyllidae such as *Calyptotrypes hihinonis*; Gryllotalpidae such as *Gryllotalpa afrcana*; and Acrididae such as *Oxya japonica*.

Examples of Collembola include Sminthuridae such as *Sminthurus viridis*; and Onychiuridae such as *Onychiurus matsumotoi*.

Examples of Isoptera include Termitidae such as *Odontotermes formosanus*, and examples of Dermaptera include Labiduridae such as *Labidura riparia*.

The following can be mentioned as examples of Arthropoda Crustacea and Arachnida.

Examples of Crustacea Isopoda include Armadillidiidae such as *Armadillidium vulgare*.

Examples of Arachnida Acarina include Tarsonemidae such as *Hemitarsonemus latus* and *Tarsaonemus pallidus*; Eupodidae such as *Penthaleus major*; Tenuipalpidae such as *Brevipalpus lewisi*; Tetranychidae such as *Tetranychus urticae, Tetranychus kanzawai, Panonychus citri*, and *Panonychus ulmi*; Eriophyidae such as *Aculus pelekassi, Aculus schlechtendali*, and *Eriophyyes chibaensis*; and Acaridae such as *Tyrophagus putrescentiae*.

As Mollusca Gastropoda, examples of Gastropoda Mesogastropoda include *Pomacea canaliculata*, and examples of Stylommatophora include *Achatina fulica, Incilaria hilineata, Milax gagates, Limax maximus*, and *Acusta despecta*.

The following may be mentioned as examples of Nematoda Secernentea and Adenophorea.

Examples of Secernentea Tylenchida include Anguimidae such as *Ditylenchus destructor*; Tylenchorhynchidae such as *Tylenchorhynchus claytoni*; Pratylenchidae such as *Pratylenchus penetrans* and *Pratylenchus coffeae*; Hoplolaimidae such as *Helicotylenchus dihystera*; Heteroderidae such as *Heterodera rostochiensis*; Meloidogynidae such as *Meloidogyne incognita*; Criconematidae such as Criconemoides; Nothotylenchidae such as *Nothotylencus acris*; and Aphelenchoidae such as *Aphelenchoides fragariae*.

Examples of Adenophorea Dorylaimida include Longidoridae such as *Xiphinema americanum*; and Trichdoridae such as *Paratrichodorus porosus*.

Furthermore, the compound of the invention is also effective for repelling, controlling, expelling pests damaging or affecting natural forest, artificial forest, trees in urban green districts, and the like. On such a scene, the following may be mentioned as specific pests. Examples of Arthropoda Insecta and Arachnida include the following.

Examples of Lepidoptera include Lymantriidae such as *Dasychira argentata* and *Lymantria disper japonica*; Lasiocampidae such as *Dendrolimus spectabilis* and *Malacosoma neustria*; Pyralidae such as *Dioryctria abietella*; Noctuidae such as *Agrotis fucosa*; Tortricidae such as *Ptycholomoides aeriferana, Laspeyresia kurokoi*, and *Cydia cryptomeriae*; Arctiidae such as *Hyphantria cunea*; Nepticulidae such as *Stigmella malella*; and Heterogeneidae such as *Parasa consocia*.

Examples of Coleoptera include Scarabaeidae such as *Anomala rufocuprea* and *Heptophylla picea*; Buprestidae such as *Agrilus spinipennis*; Cerambycidae such as *Monochamus alternatus*; Chrysomelidae such as *Lypesthes itoi*; Curculionidae such as *Scepticus griseus* and *Shirahoshizo coniferae*; Rhynchophoridae such as *Sipalinus gigas*; Scolytidae such as *Tomicus piniperda* and *Indocryphalus aceris*; and Bostrychidae such as *Rhizopertha dominica*.

Examples of Hemiptera include Aphididae such as *Cinara todocola*; Adelgidae such as *Adelges japonicus*; Diaspidiae such as *Aspidiotus cryptomeriae*; and Coccidae such as *Ceroplastes pseudoceriferus*.

Examples of Hymenoptera include Tenthredimidae such as *Pristiphora erichsoni*; Diprionidae such as *Nesodiprion japonica*; and Cynipidae such as *Dryocosmus kuriphilus*.

Examples of Dioptera include Tipulidae such as *Tipula aino*; Anthomyiidae such as *Hylemya platura*; and Cecidomyiidae such as *Contarinia inouyei* and *Contarinia matsusintome*.

Examples of Arachnida Acaria include *Oligonychus hondoensis* and *Oligonychus unuguis*.

Examples of Nematoda Secernentea Tylenchida include Paracytaphelenchidae such as *Bursaphelenchus xylophilus*.

The pest control agent containing the compound of the invention as an active ingredient can be employed as any preparation or any use form prepared by formulation effective on the above agricultural or forestry scenes, solely or in combination with or as a mixed preparation with other active compounds such as an insecticide, acaricide, nematicide, fungicide, synergist, plant regulator, herbicide, and toxic feed. The following may be mentioned as specific examples of the above other active compounds, which are not limited to the following.

Active Compounds such as insecticides or acaricides:

Examples of organophosphorus agents include Dichlorvos, Fenitorothion, Malathion, Naled, Chlorpyrifos, Diazinon, Tetrachorvinphos, Fenthion, Isoxathion, Methidathion, Salithion, Acephate, Demeton-S-methyl, Disulfoton, Monocrotophos, Azinephos-methyl, Parathion, Phosalone, Pyrimiphos-methyl, and Prothiofos. Examples of carbamete agents include Methorcarb, Fenobcarb, Propoxur, Carbaryl, Ethiofencarb, Pyrimicarb, Bendiocarb, Carbosulfan, Carbofuran, Methomyl, and Thiodicarb. Examples of organochlorine agents include Lindane, DDT, Endosulfan, Aldrin, and Chlordene. Examples of pyrethroid agents include Permethrin, Cypermethrin, Deltamethrin, Cyhalothrin, Cyfluthrin, Acrinathrin, Fenvalerate, Ethofenprox, Silafluofen, Fluvalinate, Flucythrinate, Bifenthrin, Allethrin, Phenothrin, fenpropathrin, Cyphenothrin, Furamethrin, Resmethrin, Transfurthrin, Prallethrin, Flufeneprox, Halfenprox, and Imiprothrin. Examples of neonicotinoid agents include Imidacloprid, Nitenpyram, Acetamiprid, Tefranitozine, Thiamethoxam, and Thiacloprid.

Examples of insect growth regulators such as phenylbenzoylurea include Diflubenzuron, Chlorfluazuron, Triflumuron, Flufenoxuron, Hexaflumuron, Lufenuron, Teflubenzuron, Buprofezin, Tebufenozide, Chromafenozide, Methoxyfenozide, and Cyromazine.

Examples of juvenile hormone agents include Pyriproxyfen, Fenoxycarb, methoprene, and Hydroprene.

Examples of insecticidal substances produced by microorganisms include Abamectin, Milbemectin, Nikkomycin, Emamectin benzoate, Ivermectin, and Spinosad.

Examples of other insecticides include Cartap, Bensultap, Chlorfenapyr, Diafenthiuron, Nicotine sulfate, Metaldehyde, Fipronil, Pymetrozine, Indoxacarb, and Tolfenpyrad.

Examples of acaricides includes Dicofol, Phenisobromolate, Benzomate, Tetradifon, Polynactins, Amitraz, Propargite, Fenbutatin oxide, Tricyclohexyltin hydroxide, Tebufenpyrad, Pyridaben, Fenpyroximate, Pyrimidifen, Fenazaquin, Clofentezine, Hexathiazox, Acequinocyl, Chinomethionat, Fenothiocarb, Ethoxazole, and Bifenazate.

Examples of active compounds of nematicides include methyl isocyanate, Fosthiazate, Oxamyl, and Mesulfenfos.

Examples of toxic feeds include monofluoroacetic acid, Warfarin, Coumatetralyl, and Diphacinone.

Examples of active compounds of fungicides include inorganic coppers, organic coppers, sulfur, Maneb, Thiram, Thiadiazine, Captan, Chlorothalonil, Iprobenfos, Thiophanate methyl, Benomyl, Thiabendazole, Iprodione, Procymidone, Pencycuron, Metalaxyl, Sandofan, Byleton, Triflumizole, Fenarimol, Triforine, Dithianon, Triazine, Fluazinam, Probenasole, Diethofencarb, Isoprothiolane, Pyroquilon, Iminoctadine acetate, Echlomezol, Dazomet, and Kresoxime methyl.

Examples of active compounds of synergists include bis(2,3,3,3-tetrachloropropyl) ether, N-(2-ethylhexyl) bicyclo[2.1.1]hept-5-ene-2,3-dicarboxyimide, and α-[2-(2-butoxyethoxy)ethoxy]-4,5-methylenedioxy-2-propyltoluene.

Examples of active compounds of herbicides include Bialaphos, Sethoxydim, Trifluralin, and Mefenacet. Examples of active compounds of plant regulators include indoleacetic acid, Ethephon, and 4-CPA.

Examples of active compounds of repellents include carane-3,4-diol, N,N-diethyl-m-triamide (Deet), limonene, linalool, citronellal, menthone, hinokitiol, menthol, geraniol, and eucalyptol.

The pest control agent of the invention may be employed in any forms, and the compound of the formula (1) is formulated together with auxiliaries for pesticides to produce preparations, e.g., wettable powders, wettable granules, aqueous solutions, emulsifiable concentrates, liquids, flowables including suspensions in water and emulsions in water, capsules, dusts, granules, and aerosols, which are then used. Any amount of the active ingredient may be contained in the preparations but the content is usually selected from the range of from 0.001 to 99.5% by weight as total amount of the active ingredients, being appropriately decided in accordance with various conditions such as the form of the preparation and the method of application. For example, it is preferable to produce the preparations so that the content of the active ingredients ranges about 0.01 to 90% by weight, preferably 1 to 50% by weight, in wettable powders, wettable granules, aqueous solutions, emulsifiable concentrates, liquids, flowables, capsules, and the like; about 0.1 to 50% by weight, preferably 1 to 10% by weight, in dusts and granules; or about 0.001 to 20% by weight, preferably 0.01 to 2% by weight, in aerosols.

The auxiliaries for pesticides are used for the purposes of improvement of the repelling effect, controlling effect, and expelling effect against pests, improvement of stabilization of the preparations and dispersibility, and the like, and usable examples thereof include carriers (diluents), spreaders, emulsifiers, wetting agents, dispersants, and disintegrators. Liquid carriers include water; aromatic hydrocarbons such as toluene and xylene; alcohols such as methanol, butanol and glycol; ketones such as acetone; amides such as dimethylformamide; sulfoxides such as dimethyl sulfoxide; methylnaphthalene; cyclohexane; animal or vegetable oils; and fatty acids. Examples of solid carriers are clay, kaolin, talc, diatomaceous earth, silica, calcium carbonate, montmorillonite, bentonite, feldspar, quartz, alumina, sawdust, nitrocellulose, starch, and gum arabic. General surfactants can be used as emulsifiers or dispersants. For example, anionic, cationic, nonionic or amphoteric surfactants, such as sodium higher alcohol sulfates, stearyltrimethylanmonium chloride, polyoxyethylene alkylphenyl ethers, and lauryl betaine, are useful. Further, spreaders such as polyoxyethylene nonylphenyl ether and polyoxyethylene laurylphenyl ether; wetting agents such as dialkyl sulfosuccinates; fixing agents such as carboxymethyl cellulose and polyvinyl alcohol; and disintegrators such as sodium lignin sulfonate and sodium lauryl sulfate can be used.

For example, in the case of wettable powders, a bulk powder is prepared by mixing the compound of the general formula (I) as an active ingredient, with a solid carrier, a surfactant, etc., and the bulk power can be applied after dilution to a prescribed concentration with water on use. In the case of emulsifiable concentrates, a bulk liquid is prepared by mixing the above compound as an active ingredient with a solvent, a surfactant, etc., and the bulk liquid can be applied after dilution to a prescribed concentration with water on use. In the case of dusts, a dust is prepared by mixing the above compound as an active ingredient with a solid carrier, etc. and can be applied as such. In the case of granules, a granule is prepared by mixing the above compound as an active ingredient with a solid carrier, a surface active agent, etc., followed by granulation. The granule can be applied as such. The methods for preparing the above-described preparations of various forms are not limited to the above-described methods, and one skilled in the art can optionally select an appropriate method depending on the kind of the active ingredient and the purpose of application.

The method of use varies depending on the kind and extent of pests, and the kind, cultivation form, and growth state of target crops, trees, and the like, but against Arthropods, Gastropods, Nematodes, and the like, the preparations may be generally applied in an amount of the active ingredient ranging from 0.1 to 1000 g, preferably 1 to 100 g per 10 are to the place where damage by the pests occurs or where the occurrence of damage is predicted.

With regard to specific method of application, the above wettable powders, wettable granules, aqueous solutions, emulsifiable concentrates, liquids, flowables including suspensions in water and emulsions in water, capsules, and the like may be diluted with water and sprayed onto crops, trees, and the like in an amount ranging from 10 to 1000 liter per 10 are depending on the kind, cultivation form, and growth state of target crops, trees, and the like. Furthermore, in the cases of dusts, granules, and aerosols, the preparations may be applied as such to crops, trees, and the like within the range described in the above method of use.

In the case that the target pests mainly damage crops, trees, and the like in soil, the wettable powders, wettable granules, aqueous solutions, emulsifiable concentrates, liquids, flowables including suspensions in water and emulsions in water, capsules, and the like may be, for example, diluted with water and applied generally in an amount ranging from 5 to 500 liter per 10 are. At that time, the preparations may be sprayed on the soil surface uniformly over the whole area to be applied or may be irrigated into soil. When the preparations are dusts or granules, the preparations as such may be sprayed on the soil surface uniformly over the whole area to be applied. Alternatively, at the spraying or irrigation, the preparations may be applied only to the vicinity of seeds, crops, trees, and the like to be protected from the damage by pests or the soil may be turned over during or after the spraying to disperse the active ingredient mechanically.

Furthermore, the pest control agent containing the compound of the invention as an active ingredient may be adhered around plant seeds by a known method. By such a treatment, not only damage by pests in soil can be prevented after sowing the seeds, but also stems and leaves, flowers, and fruits of plants can be protected from damage by pests.

In the case of protecting the above-described standing trees, fallen trees, processed timber, stored woods from the damage by pests such as termites or beetles, there may be mentioned methods of spraying, injecting, irrigating, or applying an oil solution, emulsifiable concentrate, wettable powder or sol, or spraying the agent in the form of a dust or granule. On such scenes, the pest control agent containing the compound of the invention as an active ingredient can be employed solely or in combination with or as a mixed preparation with other active compounds such as an insecticides, acaricide, nematicide, fungicide, repellant, and synergist.

Any amount of the active ingredient may be contained in the preparations but the content is usually in the range of 0.0001 to 95% by weight as total amount of the active ingredients. It is preferable to contain the active ingredient in an amount of 0.005 to 10% by weight in dusts, granules, and the like and in an amount of 0.01 to 50% by weight in emulsifiable concentrates, wettable powders, sols, and the like. Specifically, in the case of expelling or controlling termites or beetles, the preparations may be sprayed onto the surface of soil or timber and woods in an amount of 0.01 to 100 g per 1 $m^2$ as the amount of the active ingredient.

(B) Stock Raising and Fisheries Scenes

The pest control agent containing the compound of the invention as an active ingredient is effective for repelling, expelling, and controlling pests such as arthropods, nematodes, trematodes, cestoids, and protozoa, which are parasitic internally or externally to animals and pets raised in stock raising industry, fisheries, and homes, and the agent can be used for preventing and treating the diseases which theses pests take part in.

Target animals include spinal animals such as livestock including cattle, sheep, goat, horse, swine, and the like; cultural fishes; birds such as domestic fowls; pets and experimental animals selected from mammals including dog, cat, mouse, rat, hamster, squirrel, ferret, etc., fishes, and the like.

Among pests, the following may be mentioned as examples of Arthropoda Insecta and Arachnida. Examples of Diptera include Tabanidae such as *Chxysops japonica, Simulium iwatens*, and *Tabanus trigonus*; Muscidae such as *Ophyra leucostoma, Musca domestica*, and *Stomoxys calcitrans*; Gasterophilidae such as *Gasterophilus intestinalis*; Hypodermidae such as *Hypoderma bovis*; Calliphoridae such as *Phaenicia cuprina*; Phoridae such as *Megaseria spiracularis*; Sepsidae such as *Sepsis monostigma*; Psychodidae such as *Telmatoscopus albipunctatus* and *Psychoda alternata*; Culicidae such as *Anopheles hyrcanus sinensis, Culex tritaeniorhynchus*, and *Aedes albopictus*; Simuliidae such as *Prosilium hirtipes*; Ceratopogonidae such as *Culicoides oxystoma* and *Culicoides arakawai*.

Examples of Siphonaptera include Pulicidae such as *Ctenocephalides felis* and *Ctenocephalides canis*.

Examples of Anoplura include Echinophthiriidae such as *Haematopinus suis* and *Haematopinus eurysternus*; Trichodectidae such as *Damalinia equi*; Linognathidae such as *Linognathus vituli*; and Menoponidae such as *Menopon gallinae*.

Examples of Arthropoda Arachnida Acarina include Ixodidae such as *Haemaphysalis longicornis, Ixodes ovatus, Boophilus microplus*, and *Amblyomma testudinarium*; Macronyssidae such as *Ornithonyssus sylviarum*; Dermanyssidae such as *Dermanyssus gallinae*; Demodicidae such as *Demodex suis*; Sarcoptidae such as *Notoederes cati* and *Sarcoptes sylvianum*; and Psoroptidae such as *Otodectes cynotis* and *Psoroptes bovis*.

As examples of Nematoda Phasmidia, the following may be mentioned.

Examples of Strongylida include Ancylostoma, *Stephanurus dentatus, Metastrongylus elongatus*, Trichostrongylus, and Oesophagostomum.

Examples of Platyhelminthes Trematoda include *Schistosoma japonicum, Fasciola hepatica, Paramphistomum cervi, Paragonimus westermanii*, and *Prosthogonimus japonicus*.

Examples of Cestoda include *Anoplocephala perfoliata, Moniezia expansa, Moniezia benedeni, Raillietina tetragona*, Raillietina sp., and *Raillietina cesticillus*.

Examples of Protozoa Mastigophora include Histomonas and the like as Rhizomastigida, Leishmania, Trypanosoma, and the like as Tripanpsomidae, Giardia and the like as Polymastigida, and Trichomonas and the like as Trichomonadia.

Furthermore, examples of Sarcodina Amoebida include Entamoeba, examples of Sporozoa Piroplasmea include Theilaria, and Babesia, and examples of Telosporidia include Eimeria, Plasmodium, and Toxoplasma.

The pest control agent containing the compound of the invention as an active ingredient can be employed as any preparation or any use form prepared by formulation effective on the above agricultural or forestry scenes, solely or in combination with or as a mixed preparation with other active compounds such as an insecticide, acaricide, nematicide, fungicide, synergist, plant regulator, herbicide, and toxic feed. The substances mentioned in the article of "(A) Agricultural and forestry scenes" may be mentioned as specific examples of the above other active compounds, but they are not limited thereto.

The specific application methods include incorporation into feeds of livestock, pets, and the like; oral administration as a suitable orally-ingestable formulated composition, e.g., a tablet, pill, capsule, paste, gel, drink, medicated feed, medicated drink, medicated additional feed, sustained release large pill, or sustained release device so as to be retained in gastrointestinal tracts containing a pharmaceutically acceptable carrier and a coating substance; and percutaneous application as a spay, powder, grease, cream, ointment, emulsion, lotion, preparation for spot-on, preparation for pour-on, shampoo, or the like.

As the methods for percutaneous application and topical application, devices (e.g., collars, medallions, and ear-tags) attached to animals so as to control arthropods topically or systemically may be utilized.

The following will illustrate specific methods for oral administration and percutaneous application in the case of use for anthelmintics, but in the invention, the methods of application are not limited to the following descriptions.

In the case of oral administration as a medicated drink, a suspension or dispersion may be usually formed by dissolving an active ingredient into an appropriate non-toxic solvent or water together with a suspending agent such as bentonite, a wetting agent, or other excipients, and an antifoaming agent may be contained, if necessary. The drink generally contain the active ingredient in an amount of 0.01 to 1.0% by weight, preferably 0.01 to 0.1% by weight.

In the case of oral administration as unit use forms of dry solid, a capsule, pill, or tablet containing a predetermined amount of the active ingredient is usually employed. These use forms may be prepared by mixing the active ingredient homogeneously with a suitably pulverized diluent, filler, disintegrator, and/or binders such as starch, lactose, talc, magnesium stearate, plant gum, and the like. At the formulation of such unit use forms, the quantity and content of an anthelmintic may be optionally determined depending on the kind of host animal to be treated, the kind of parasite, and the body weight of the host.

In the case of administration as a feed, there may be mentioned methods wherein the compound of the active ingredient is homogeneously dispersed in the feed, the agent is employed as top-dressing or in a form of pellet. For achieving an anthelmintic effect, the compound of the active ingredient is contained in the final feed in an amount of 0.0001 to 0.05% by weight, preferably 0.0005 to 0.01% by weight.

In the case of a solution or dispersion in a liquid carrier excipient, the preparations may be administered parenterally to animals by injection to proventriculus, or intramuscular, endotracheal, or subcutaneous injection. Because of parenteral administration, the compound of the active ingredient is preferably mixed with a vegetable oil such as peanuts oil or cottonseed oil. In such formulation, the compound of the active ingredient is generally contained in an amount of 0.05 to 50% by weight, preferably 0.1 to 0.2% by weight. Moreover, the preparation mixed with a carrier such as dimethyl sulfoxide, a hydrocarbon solvent, or the like can be applied directly and topically to the outer surface of livestocks or pets by spraying or direct pouring.

(C) Public Health Scenes

The pest control agent containing the compound of the invention as an active ingredient is also effective for repelling, expelling, and controlling pests on public health scenes which adversely affect the environment of food, clothing and shelter, or further damage human bodies or transporting or carrying pathogens, for the purpose of keeping public health conditions. Specifically, the pest control agent of the invention is effective for repelling, expelling, and controlling lepidopteran, coleopteran, bookworms, cockroaches, flies, and mites which damage houses themselves and indoor or outdoor timber, wood products such as wood furniture, stored foods, clothes, books, animal goods (leather, fur, wool, feathers, etc.), plant goods (clothes, paper, etc.), and the like, and adversely affect healthy life. The following will illustrate specific examples of pests on such public health scenes.

As Arthropoda Insecta, the following may be mentioned. Examples of Lepidoptera include Lymantriidae such as *Euproctis similis*; Lasiocampidae such as *Dendrolimus undans flaveola*; Heterogeneidae such as *Parasa consocia*; Zygaenidae such as *Artona funeralis*; Pyralidae such as *Cadra cautella, Ephestia cautella*, and *Plodia interpunctella*; Gelechiidae such as *Sitotroga cerearella*; Tineidae such as *Tinea pellionella* and *Tineola bisselliella*.

Examples of Coleoptera include Oedemeridae such as *Xanthochroa waterhousei*; Meloidae such as *Epicauta gorhami*; Staphylimidae such as *Paederus fuscipes*; Rhynchophoridae such as *Sitophilus zeamais* and *Sitophilus oxyzae*; Bruchidae such as *Callosobruchus chinensis, Bruchus pisorum*, and *Bruchus rufimanus*; Tenebrionidae such as *Tribolium castaneum*; Cucujidae such as *Oryzoephilus surinamensis* and *Placonotus testaceus*; Anobiidae such as *Lasioderma serricorne* and *Stegobium paniceum*; Dermestidae such as *Attagenus unicolor, Anthrenus verbasci*, and *Dermestes maculatus*; Ptimidae such as *Gibbium aequinoctiale*; Bostrychidae such as *Dinoderus minutus* and *Rhizopertha dominica*; and Lyctidae such as *Lyctus brunneus*.

Examples of Hymenoptera include Vespidae such as *Vespa mandarinia*; Formicidae such as *Brachyponera chinensis*; and Pompilidae such as *Batozonellus annulatus*.

Examples of Diptera include Culicidae such as *Aedes jaonica*; Ceratopogonidae such as *Culicoides sp.*; Chironomidae such as *Chironomus dorsalis*; Simuliidae such as *Simulium aokii*; Tabanidae such as *Chrysops japonicus*; Muscidae such as *Musca domestica*; Anthomyiidae such as *Fannia canicularis*; Calliphoridae such as *Phormia regina*; Sarcophagidae such as *Boettcherisca peregrina*; Drosophilidae such as *Drosophila virilis*; and Piophilidae such as *Piophila casei*.

Examples of Siphonaptera include Pulicidae such as *Pulex irritans*.

Examples of Collembola include Neogastruridae such as *Neogastruna communis*.

Examples of Blattaria include Blattellidae such as *Blattela germania* and *Asiablatta kyotensis*; and Blattidae such as *Periplaneta americana, Periplaneta fuliginosa*, and *Periplaneta japonica*.

Examples of Orthoptera include Gryllacridoidea such as *Diestrammena japonica* and Steropelmatidae.

Examples of Anoplura include Pediculidae such as *Pediculus humanus capitis*; and Pthiridae such as *Pthirus pubis*.

Examples of Hemiptera include Cimicidae such as *Cimex lectularius*; and Reduriidae such as *Isyndus obscurus*.

Examples of Isoptera include Phinotermitidae such as *Reticulitermes speratus* and *Coptotermes formosanus*; and Kalotermitidae such as *Crytotermes domesticus*, and examples of Psocoptera include Trogiidae such as *Lepinotus reticulatus*; and Liposcelidae such as *Liposcelis bostrichophilus*. Examples of Thysanura include Lepismatidae such as *Ctenolepisma villosa* and *Lepisma saccharina*.

As examples of *Arthropoda Arachnida*, the following may be mentioned.

Examples of Acarina include Ixodidae such as *Ixodes persulcatus*; Macronyssidae such as *Ornithonyssus bacoti*; Cheyletidae such as *Chelacaropsis moorei*; Pyemotidae such as *Pyemotes tritici*; Demodicidae such as *Demodex folliculorum*; Pyroglyphidae such as *Permatophagoides pteronyssius*; Sarcoptidae such as *Sarcoptes scabiei*; Trombiculidae such as *Leptotrombidum akamushi*; Acaridae such as *Tyrophagus putrescentiae* and *Lardoglyphus konoi*; and Carpoglyphidae such as *Carpoglyphus lactis*.

Examples of Araneae include Clubionidae such as *Chiracanthium japonicum*; Heteropodidae such as *Heteropoda venatoria*; Pholcidae such as *Spezmophora senoculata* and *Pholcus phalangioides*; Urocteidae such as *Uroctea copactilis*; and Salticidae such as *Plexippus paykulli* and *Plexippus setipes*.

Examples of Scorpiones include Buthidae such as *Isometrus europaeus*.

As other Arthropoda, examples of *Chilopoda Scolopendromorpha* include Scolopendridae such as *Scolopendra subspinipes* and *Otostigmus multispinosus*, and examples of Scutigeromorpha include Scutigeridae such as *Thereuonema hilgendorfi*. Moreover, examples of Arthropoda Diplopoda Polydesmoidea include Strongylosomidae such as *Oxidus gracilis*, and examples of *Arthropoda Crustacea Isopoda* include Oniscidae such as *Porcellio scaber*. Furthermore, examples of Annelida Hirudinea Gnathobdellida include Haemadipsidae such as *Haemadipsa zeylanica japonica*.

The pest control agent containing the compound of the invention as an active ingredient can be employed as any preparation or any use form prepared by formulation effective on the above public health scenes, solely or in combination with or as a mixed preparation with other active compounds such as an insecticide, acaricide, nematicide, fungicide, synergist, plant regulator, herbicide, and toxic feed. The substances mentioned in the article of "(A) Agricultural and forestry scenes" may be mentioned as specific examples of the above other active compounds, but they are not limited thereto.

The use form of the pest control agent of the invention may be any form and the protection of the above animal goods or plant goods can be achieved by spraying an oil solution, emulsifiable concentrate, wettable powder, dust, or the like, placing a resin steam-fogging agent, treating with a smoking agent or aerosol, placing a granule, tablet, or toxic feeds spraying an aerosol, or the like. The compound of the active ingredient is preferably contained in the preparations in an amount of 0.0001 to 95% by weight.

As application method, against pests, for example, directly damaging arthropods, disease-carrying arthropods, and the like, there may be mentioned methods of spraying, injecting, irrigating, and applying an oil solution, emulsifiable concentrate, wettable powder, or the like, spraying a dust or the like, treating with a preparation such as a fumigant, mosquito coil, heat aerosol including self-combustion type smoking agent or chemically reactive aerosol, smoking agent including fogging, or ULV agent, and others. Alternatively, a granule, tablet, or toxic feed, for example, may be placed as other form, or a floating dust, granule, or the like may be applied by adding them dropwise into waterways, wells, reservoirs, water tanks, and other running water or retained water.

Furthermore, Oriental tussock moths which are also pests in agriculture and forestry can be controlled in a similar manner to the methods described in the article of "(A) Agricultural and forestry scenes". Method of incorporating the control agent into the feed of livestock so that the dung is contaminated with the active ingredient is effective against flies, and method of vaporization into air by means of an electric mosquito coil is also effective against mosquitoes.

The preparations which are use forms thereof may be present as mixed preparations together with the above-described other active compound such as an insecticide, acaricide, nematicide, fungicide, repellant, or synergist, and the compound of the active ingredient is preferably contained in these preparations in an amount of 0.0001 to 95% by weight in total. By the way, it is also possible to use the preparations in combination with other active compounds on use.

In the case of protecting houses, wood furniture, and the like from damage by pests such as termites or beetles, there may be mentioned methods of spraying, injecting, irrigating, or applying an oil solution, emulsifiable concentrate, wettable powder or sol, or spraying the agent in the form of a dust or granule toward houses, wood furniture, and the like and vicinity thereof. On such scenes, the compound of the invention can be employed solely or in combination with or as a mixed preparation with other active compounds such as an insecticide, acaricide, nematicide, fungicide, repellant, and synergist.

Any amount of the compound of the active ingredient such as the compound of the invention may be contained in the preparations but the content is usually in the range of 0.0001 to 95% by weight as total amount of the active ingredients. It is preferable to contain the compounds in an amount of 0.005 to 10% by weight in oil solutions, dusts, granules, and the like and in an amount of 0.01 to 50% by weight in emulsifiable concentrates, wettable powders, sols, and the like. Specifically, in the case of expelling or controlling termites or coleopteran, the preparations may be sprayed to the vicinity or directly onto the surface in an amount of 0.01 to 100 g per 1 $m^2$ as the amount of the compound of the active ingredient.

At repelling, expelling, and controlling pests which damage human bodies or transport or carry pathogens, other than the above-described methods, there may be mentioned oral administration as a suitable orally-ingestable formulated composition, e.g., a tablet, pill, capsule, paste, gel, drink, medicated feed, medicated drink, medicated additional feed, sustained release large pill, or sustained release device so as to be retained in gastrointestinal tracts containing a pharmaceutically acceptable carrier and a coating substance; and percutaneous application as a spay, powder, grease, cream, ointment, emulsion, lotion, preparation for spot-on, preparation for pour-on, shampoo, or the like. Specific formulation can be carried out in a similar manner to the methods mentioned in the articles of "(B) Stock raising and fisheries scenes".

Best Mode for Carrying Out the Invention

The following will explain the present invention in further detail with reference to Examples but the invention is not limited to the following Examples unless it exceeds the gist thereof.

EXAMPLE 1

Production of 1-(2,6-dichloro-4-trifluoromethylphenyl)-4-trifluoromethylsulfinyl-5-(pyrazin-2-ylmethylamino)pyrazole-3-carbonitrile (Compound No. 5)

To a mixture of 10.0 g of 5-amino-1-(2,6-dichloro-4-trifluoromethylphenyl)-4-trifluoromethylsulfinylpyrazole- 3-carbonitrile, 2.5 g of formylpyrazine, and 80 ml of toluene was added 0.1 g of p-toluenesulfonic acid monohydrate, and the whole was heated under reflux for 10 hours while the resulting water was removed. After cooling to room temperature, 30 ml of ice-water was added thereto, followed by extraction. The organic layer was dried over anhydrous sodium sulfate. The solvent was remove by distillation under reduced pressure to obtain crude 1-(2,6-dichloro-4-trifluoromethylphenyl)-4-trifluoromethylsulfinyl-5-(pyrazin-2-ylmethylideneimino)pyrazole-3-carbonitrile.

To a methanol (100 ml) solution of 1-(2,6-dichloro-4-trifluoromethylphenyl)-4-trifluoromethylsulfinyl-5-(pyrazin-2-ylmethylideneimino)pyrazole-3-carbonitrile obtained in the above was gradually added 0.9 g of sodium borohydride. After 1 hour of stirring at room temperature, ice and ethyl acetate were added thereto, followed by extraction. The organic layer was washed with saturated saline and then dried over anhydrous sodium sulfate. The residue was purified by a silica gel column chromatography to obtain 7.0 g of the compound (No. 5) described in the following Table 1. Melting point: 169° C.

$^1$HNMR (CDCl$_3$): 4.37 (2H, m), 6.81 (1H, m), 7.74 (2H, d), 8.39 (1H, d), 8.50 (2H, m)

EXAMPLE 2

Production of 1-(2,6-dichloro-4-trifluoromethylphenyl)-4-methylsulfinyl-5-(pyrazin-2-ylmethylamino)pyrazole-3-carbonitrile (Compound No. 1)

To a mixture of 5.6 g of 5-amino-1-(2,6-dichloro-4-trifluoromethylphenyl)-4-methylsulfinylpyrazole-3-carbonitrile, 2.0 g of formylpyrazine, and 60 ml of toluene was added 20 mg of p-toluenesulfonic acid monohydrate, and the whole was heated under reflux for 3 hours while the resulting water was removed. After cooling to room temperature, 0.1 ml of triethylamine and 30 ml of ice-water were added thereto, followed by extraction. The organic layer was dried over anhydrous sodium sulfate. The solvent was remove by distillation under reduced pressure to obtain crude 1-(2,6-dichloro-4-trifluoromethylphenyl)-4-methylsulfinyl-5-(pyrazin-2-ylmethylideneimino)pyrazole-3-carbonitrile.

To a methanol (50 ml) solution of 1-(2,6-dichloro-4-trifluoromethylphenyl)-4-methylsulfinyl-5-(pyrazin-2-ylmethylideneimino)pyrazole-3-carbonitrile obtained in the above was gradually added 0.7 g of sodium borohydride. After 1 hour of stirring at room temperature, ice and ethyl acetate were added thereto, followed by extraction. The organic layer was washed with saturated saline and then dried over anhydrous sodium sulfate. The residue was purified by a silica gel column chromatography to obtain 5.1 g of the compound (No. 1) described in the following Table 1. Melting point: 198° C.

$^1$HNMR (CDCl$_3$): 3.33 (3H, s), 4.18 (2H, d), 7.15 (1H, t), 7.71 (2H, s), 8.41 (2H, d), 8.51 (1H, d)

EXAMPLE 3

Production of 1-(2,6-dichloro-4-trifluoromethylphenyl)-4-trifluoromethylsulfinyl-5-(1-oxy-pyridin-3-ylmethylamino)pyrazole-3-carbonitrile (Compound No. 14)

In 10 ml of N,N-dimethylformamide was suspended 0.1 g of 60% sodium hydride, and 1 g of 5-amino-1-(2,6-dichloro-4-trifluoromethylphenyl)-4-trifluoromethylsulfinylpyrazole-3-carbonitrile was gradually added thereto. After 20 minutes of stirring at room temperature, 3 drops of 15-crown-5-ether and then 0.3 g of 3-chloromethylpyridine-1-oxide were added thereto, followed by stirring at room temperature. After standing over one night, water and ethyl acetate were added thereto and the mixture was neutralized by 1N hydrochloric acid. After liquid separation, the organic layer was washed with saturated saline and then dried over anhydrous sodium sulfate. The residue was purified by a silica gel column chromatography to obtain 0.9 g of the compound (No. 14) described in the following Table 1. Melting point: 189–191° C.

$^1$HNMR (CDCl$_3$): 4.2–4.5 (2H, m), 7.03 (1H, d), 7.12 (1H, t), 7.18 (1H, t), 7.74 (2H, s), 8.03 (2H, m)

EXAMPLE 4

Production of N-[3-cyano-1-(2,6-dichloro-4-trifluoromethylphenyl)pyrazole-5-yl]pyrazine-2-carboxamide Into a mixture of 0.5 g (1.6 mmol) of 5-amino-1-(2,6-dichloro-4-trifluoromethylphenyl)pyrazole-3-carbonitrile, 0.24 g (1.7 mmol) of methyl pyrazinecarboxylate, and 0.5 ml of acetonitrile was gradually added 0.3 g (1.6 mmol) of 28% CH$_3$ONa/CH$_3$OH at room temperature. After 2 hours of stirring at room temperature, 5 ml of water and then concentrated hydrochloric acid were added thereto to make the mixture pH 2, whereby crystals were precipitated. Thereto was added 10 ml of ethyl acetate, followed by extraction. The organic layer was washed with saturated saline and then dried over anhydrous sodium sulfate. After removal of the sodium sulfate by filtration, the layer was concentrated and the resulting crystals were filtrated. The crystals were washed with a small amount of hexane and ethyl acetate and the dried to obtain 0.5 g (yield 77%) of N-[3-cyano-1-(2,6-dichloro-4-trifluoromethylphenyl)pyrazole-5-yl]pyrazine-2-carboxamide.

EXAMPLE 5

Production of 1-(2,6-dichloro-4-trifluoromethylphenyl)-5-(pyrazin-2-ylchloromethylimino)pyrazole-3-carbonitrile A mixture of 139 g (0.33 mol) of N-[3-cyano-1-(2,6-dichloro-4-trifluoromethylphenyl)pyrazole-5-yl]pyrazine-2-carboxamide, 72.6 g (0.35 mol) of phosphorus pentachloride, and 300 ml of toluene was heated under reflux for 2 hours. Further, 5 g of phosphorus pentachloride was added thereto, followed by heating under reflux for 1 hour. The mixture was cooled to room temperature and allowed to stand overnight. After stirring for 30 minutes, crystals were filtrated and washed with toluene. The crystals were dissolved in 1 L of chloroform and the solution was extracted after the addition of water. The organic layer was washed twice with water, and with saturated saline, and then, dried over anhydrous sodium sulfate. The solvent was removed by distillation and the resulting crystals were washed with hexane to obtain 112.3 g (yield 79%) of 1-(2,6-dichloro-4-trifluoromethylphenyl)-5-(pyrazin-2-ylchloromethylimino)pyrazole-3-carbonitrile.

EXAMPLE 6

Production of 1-(2,6-dichloro-4-trifluoromethylphenyl)-5-(pyrazin-2-ylmethylamino)pyrazole-3-carbonitrile To an ethanol (2 ml) suspension of 85 mg (2.2 mmol) of sodium borohydride was gradually added 0.5 g (1.1 mmol)

of 1-(2,6-dichloro-4-trifluoromethylphenyl)-5-(pyrazin-2-ylchloromethylimino)pyrazole-3-carbonitrile at 20° C. or less. After 1 hour of stirring at room temperature, the mixture was gradually poured into 40 ml of water to precipitate crystals. After 30 minutes of stirring, the crystals were filtered and washed with water until the pH of the filtrate became 6. The crystals thus obtained were dissolved in ethyl acetate and the solution was extracted after the addition of saturated saline. The organic layer was dried over anhydrous magnesium sulfate, filtrated, and concentrated. The resulting crystals were filtered, washed with a small amount of hexane and ethyl acetate, and dried to obtain 0.42 g (yield 92%) of 1-(2,6-dichloro-4-trifluoromethylphenyl)-5-(pyrazin-2-ylmethylamino)pyrazole-3-carbonitrile.

EXAMPLE 7

Production of 1-(2,6-dichloro-4-trifluoromethylphenyl)-4-trifluoromethylsulfenyl-5-(pyrazin-2-ylmethylamino)pyrazole To a solution of 3.0 g of 1-(2,6-dichloro-4-trifluoromethylphenyl)-5-(pyrazin-2-ylmethylamino)pyrazole dissolved in 30 ml of dried methylene chloride under a nitrogen atmosphere was added 14 ml of dried methylene chloride solution of trifluoromethylsulfenyl chloride at room temperature over about 1 hour, followed by stirring overnight. Saturated aqueous sodium hydrogen carbonate solution was added thereto, and the organic layer was washed with saturated aqueous sodium hydrogen carbonate solution and water several times. Thereafter, the layer was purified by a silica gel column chromatography. After removal of solvent, drying in vacuo afforded 3.59 g of 1-(2,6-dichloro-4-trifluoromethylphenyl)-4-trifluoromethylsulfenyl-5-(pyrazin-2-ylmethylamino)pyrazole.

EXAMPLE 8

Production of 1-(2,6-dichloro-4-trifluoromethylphenyl)-4-trifluoromethylsulfinyl-5-(pyrazin-2-ylmethylamino)pyrazole-3-carbonitrile Into 1.0 ml of 1,2-dichloroethane were suspended 234 mg (1.3 mmol) of potassium trifluoromethanesulfinate, 358 mg (1.6 mmol) of dimethylamine p-toluenesulfonate, 413 mg (1.0 mmol) of 1-(2,6-dichloro-4-trifluoromethylphenyl)-5-(pyrazin-2-ylmethylamino)pyrazole-3-carbonitrile, and then 301 mg (2.5 mmol) of thionyl chloride was added under ice-cooling. The mixture was warmed to 60° C. and stirred for 30 minutes. Thereafter, the reaction mixture was analyzed by a high-performance liquid chromatograph to observe the formation of 1-(2,6-dichloro-4-trifluoromethylphenyl)-4-trifluoromethylsulfinyl-5-(pyrazin-2-ylmethylamino)pyrazole-3-carbonitrile in 11% yield. The conversion of 1-(2,6-dichloro-4-trifluoromethylphenyl)-5-(pyrazin-2-ylmethylamino)pyrazole-3-carbonitrile was found to be 95%.

EXAMPLE 9

Production of 1-(2,6-dichloro-4-trifluoromethylphenyl)-4-trifluoromethylsulfenyl-5-(pyrazin-2-ylmethylamino)pyrazole-3-carbonitrile Into 5.0 ml of 1,2-dichloroethane were suspended 1.725 g (10.0 mmol) of potassium trifluoromethanesulfinate, 895 mg (4.1 mmol) of dimethylamine p-toluenesulfonate, 951 mg (5.0 mmol) of p-toluenesulfonic acid monohydrate, and then 1.506 g (12.6 mmol) of thionyl chloride was added under ice-cooling. After 3 hours of stirring at room temperature, 1.03 g (2.5 mmol) of 1-(2,6-dichloro-4-trifluoromethylphenyl)-5-(pyrazin-2-ylmethylamino)pyrazole-3-carbonitrile was added thereto, and the mixture was warmed to 40° C. and stirred for 5 hours. The reaction mixture was neutralized with saturated aqueous sodium hydrogen carbonate solution and then extracted with dichloromethane. The organic layer was dried over anhydrous magnesium sulfate. The solvent was removed by distillation under reduced pressure and the resulting oil was purified to isolate 487 mg (yield 38%) of 1-(2,6-dichloro-4-trifluoromethylphenyl)-4-trifluoromethylsulfenyl-5-(pyrazin-2-ylmethylamino)pyrazole-3-carbonitrile.

EXAMPLE 10

Production of 1-(2,6-dichloro-4-trifluoromethylphenyl)-4-trifluoromethylsulfenyl-5-(pyrazin-2-ylmethylamino)pyrazole-3-carbonitrile In 350 ml and 110 ml of acetonitrile were dissolved 7.89 g (8.88 mmol) of bis(1-(2,6-dichloro-4-trifluoromethylphenyl)-3-carbonitrile-5-(pyrazin-2-ylmethylamino)pyrazol-4-yl)-disulfide, 5.44 g (31.6 mmol) of potassium trifluoromethylsulfinate, and 0.40 g (1.24 mmol) of dioxobis(acetylacetonato)molybdenum, and then 3.4 ml (27.2 mmol) of 80% t-butyl hydroperoxide solution was added dropwise thereto at room temperature. Furthermore, every 4 hours, the addition of 5.44 g (31.6 mmol) of potassium trifluoromethylsulfinate and 3.4 ml (27.2 mmol) of 80% t-butyl hydroperoxide solution was repeated twice, followed by stirring for 15 hours at room temperature. Then, 5.44 g (31.6 mmol) of potassium trifluoromethylsulfinate and 3.4 ml (27.2 mmol) of 80% t-butyl hydroperoxide solution were again added, followed by stirring for 6 hours. After removal of precipitated pale brown crystals by filtration, acetonitrile was removed from the filtrate by distillation under reduced pressure and ethyl acetate was added, followed by extraction. After washing of the organic layer with water, the solvent was removed under reduced pressure and the residue was subjected to a column chromatographic purification (Hex/AcOE$_2$=5/2) to obtain 0.88 g (1.7 mmol) of pale yellow crystals of 1-(2,6-dichloro-4-trifluoromethylphenyl)-4-trifluoromethylsulfenyl-5-(pyrazin-2-ylmethylamino)pyrazole-3-carbonitrile in 9.6% yield.

EXAMPLE 11

Production of 1-(2,6-dichloro-4-trifluoromethylphenyl)-4-trifluoromethylsulfenyl-5-(pyrazin-2-ylmethylamino)pyrazole-3-carbonitrile Under a nitrogen atmosphere, 10.1 mg (0.24 ml) of sodium borohydride was added to a methanol (1.5 ml) solution of 50 mg (0.11 mmol) of 1-(2,6-dichloro-4-trifluoromethylphenyl)-4-thiocyanato-5-(pyrazin-2-ylmethylamino)pyrazole-3-carbonitrile, followed by stirring at room temperature for 2 hours. After removal of the solvent from the reaction mixture by distillation under reduced pressure, 2 ml of DMF was added under nitrogen. After cooling in a dry ice-acetone bath, a DMF (0.5 ml) solution of 54.5 mg (0.11 mmol) of MEC-12, a trifluoromethylating agent manufactured by Daicel Chemical Industries, Ltd. was added thereto. After 1 hour of stirring at room temperature, ethyl acetate and water were added, followed by extraction. The organic layer was subjected to an LC analysis to observe the formation of 1-(2,6-dichloro- 4-trifluoromethylphenyl)-4-trifluoromethylsulfenyl-5-(pyrazin-2-ylmethylamino)pyrazole-3-carbonitrile in 41.7 area % yield.

The compounds described in Table 1 were synthesized in accordance with the methods described in Examples 1 to 11. The following show Compound Nos. and NMR data.

No. 2
$^1$HNMR (CDCl$_3$): 3.33 (3H, s), 4.19 (2H, d), 7.15 (1H, bt), 7.71 (2H, s), 8.40 (1H, d), 8.42 (1H, d), 8.51 (1H, d)

No. 3
$^1$HNMR (CDCl$_3$): 1.39 (3H, t), 3.26 (2H, m), 4.34 (2H, d), 6.83 (1H, t), 7.68 (2H, d), 8.35 (1H, d), 8.47 (1H, d), 8.51 (1H, s)

No. 4
$^1$HNMR (CDCl$_3$): 4.43 (2H, d), 6.75 (1H, t), 6.78 (1H, t), 7.75 (2H, d), 8.41 (1H, m), 8.50 (2H, m)

No. 6
$^1$HNMR (CDCl$_3$): 2.56 (3H, s), 4.30 (2H, m), 6.62 (1H, bm), 7.72 (2H, d), 8.25 (1H, d), 8.35 (1H, d)

No. 7
$^1$HNMR (CDCl$_3$): 4.66 (2H, d), 5.27 (1H, brs), 5.30 (1H, s), 5.61 (1H, s), 7.76 (2H, s), 8.41 (1H, d), 8.49 (1H, d), 8.54 (1H, s)

No. 8
$^1$HNMR (CDCl$_3$): 4.53 (2H, s), 6.88 (1H, t), 7.71 (2H, s), 8.29 (1H, s), 8.36 (1H, s), 8.39 (1H, s)

No. 9
$^1$HNMR (CDCl$_3$): 4.35 (2H, m), 6.85 (1H, bs), 7.23 (1H, d), 7.74 (2H, d), 8.69 (1H, d), 9.01 (1H, s)

No. 10
$^1$HNMR (CDCl$_3$): 2.37 (3H, s), 4.90 (2H, d), 5.27 (1H, m), 7.45 (2H, m), 7.75 (2H, s), 9.12 (1H, dd)

No. 11
$^1$HNMR (CDCl$_3$): 4.68 (2H, m), 6.71 (1H, bs), 7.47 (1H, d), 7.73 (1H, d), 9.11 (1H, d)

No. 12
$^1$HNMR (CDCl$_3$): 4.1–4.5 (2H, m), 6.69 (1H, t), 7.10 (2H, d) 7.21 (1H, t), 7.77 (2H, s), 8.10 (2H, d)

No. 13
$^1$HNMR (CDCl$_3$): 4.3 (2H, m), 7.02 (2H, d) 7.70 (2H, s), 8.01 (2H, d)

No. 15
$^1$HNMR (CDCl$_3$): 4.84 (2H, d), 6.35 (1H, brs), 7.31 (3H, m), 7.77 (2H, s), 8.15 (1H, m)

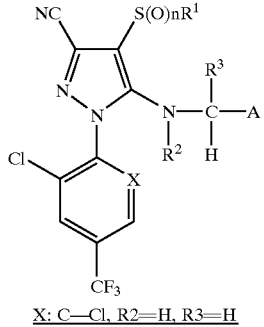

X: C—Cl, R2=H, R3=H

| Compound No. | S(O)nR$^1$ | A | m.p.(° C.) |
|---|---|---|---|
| 1 | SOCH$_3$ | 3-pyrazinyl | 198 |

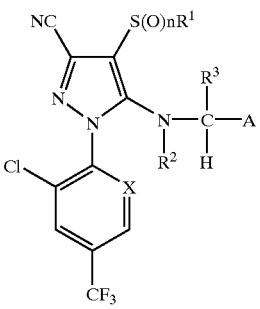

X: C—Cl, R2=H, R3=H

| Compound No. | S(O)nR$^1$ | A | m.p.(° C.) |
|---|---|---|---|
| 2 | SO$_2$CH$_3$ | 3-pyrazinyl | 147–149 |
| 3 | SOC$_2$H$_5$ | 3-pyrazinyl | 158–162 |
| 4 | SOCHF$_2$ | 3-pyrazinyl | 178 |
| 5 | SOCF$_3$ | 3-pyrazinyl | 169 |
| 6 | SOCF$_3$ | 5-methyl-2-pyrazinyl | 186–888 |
| 7 | SCH$_2$F | 3-pyrazinyl | 119–120 |
| 8 | SCHF$_2$ | 3-pyrazinyl | 117–118 |
| 9 | SOCF$_3$ | 4-pyrimidinyl | 101–103 |
| 10 | SCH$_3$ | 3-pyridazinyl | 151–153 |
| 11 | SOCF$_3$ | 3-pyridazinyl | 79–81 |
| 12 | SOCHF$_2$ | 4-pyridyl N-oxide | 202–204 |

-continued

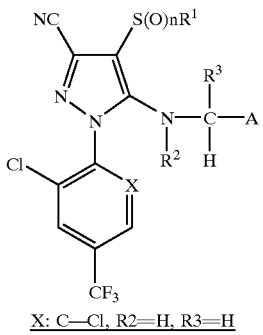

X: C—Cl, R2=H, R3=H

| Compound No. | S(O)nR¹ | A | m.p.(° C.) |
|---|---|---|---|
| 13 | SOCF$_3$ | (4-pyridyl N→O) | 179 |
| 14 | SOCF$_3$ | (3-pyridyl N→O) | 189–191 |
| 15 | SOCF$_3$ | (2-pyridyl N→O) | 183–185 |

The following will illustrate Formulation Examples of the agricultural and horticultural insecticides containing the compound of the invention as an active ingredient but the use forms are not limited to the following.

<Formulation Example 1> Wettable Powder

Twenty parts by weight of the compound of the invention, 20 parts by weight of Carplex #80 (a product name of the white carbon manufactured by Shionogi & Co., Ltd.), 52 parts by weight of ST Kaolin Clay (a product name of the kaolinite manufactured by Tsuchiya Kaolin K.K.), 5 parts by weight of Sorpol 9047K (a product name of the anionic surfactant manufactured by Toho Chemical Industry Co., Ltd.), and 3 parts by weight of Runox P65L (a product name of the anionic surfactant manufactured by Toho Chemical Industry Co., Ltd.) were mixed and ground uniformly to obtain a wettable powder containing 20% by weight of the active ingredient.

<Formulation Example 2> Dust

Two parts by weight of the compound of the invention, 93 parts by weight of clay (manufactured by Nippon Talc K.K.), and 5 parts by weight of Carplex #80 (a product name of the white carbon manufactured by Shionogi & Co., Ltd.) were uniformly mixed and ground to obtain a dust containing 2% by weight of the active ingredient.

<Formulation Example 3> Emulsifiable Concentrate

In a mixed solvent of 35 parts by weight of xylene and 30 parts by weight of dimethylformamide was dissolved 20 parts by weight of the compound of the invention, and 15 parts by weight of Sorpol 3005X (a product name of a mixture of a nonionic surfactant and an anionic surfactant, available from Toho Chemical Co., Ltd.) was added thereto to obtain an emulsifiable concentrate containing 20% by weight of the active ingredient.

<Formulation Example 4> Flowable

A mixture of 30 parts by weight of the compound of the invention, 5 parts by weight of Sorpol 9047K, 3 parts by weight of Sorbon T-20 (a product name of the nonionic surfactant manufactured by Toho Chemical Co., Ltd.), 8 parts by weight of ethylene glycol, and 44 parts by weight of water were wet ground in Dynomill (manufactured by Shinmaru enterprises Co.). To the resulting slurry was added 10 parts by weight of a 1 wt % aqueous solution of xanthan gum (naturally occurring polymer), followed by mixing and grinding thoroughly to obtain a flowable containing 20% by weight of the active ingredient.

The following will illustrate Test Examples of the agricultural and horticultural insecticides containing the compound of the invention as an active ingredient but the use forms are not limited to the following.

Test Example 1

Insecticidal Effect on Larvae of Brown Rice Planthopper (*Nilaparvata lugens*)

A rice seedling was planted in a glass cylinder (inner diameter: 3 cm×length: 17 cm), and five 4th instar larvae of brown rice planthopper were set free therein. An agricultural and horticultural insecticide of the invention was prepared in accordance with Formulation Example 3 and diluted with water, and 0.5 ml of the resulting emulsion was sprayed into the cylinder by means of a spraying tower (manufactured by Mizuho Rika) (duplicates at a concentration). The cylinder was kept in a constant temperature room at 25° C., and the mortality and agony of the larvae were examined after 5 days from the treatment to obtain a death rate (%) taking an agonizing insect as a ½ dead insect. The results obtained are shown in Table 2 (the compound numbers in Table 2 correspond to the numbers in Table 1).

TABLE 2

| Compound No. | Concentration (ppm) | Death Rate (%) |
|---|---|---|
| 1 | 500 | 100 |
| 3 | 500 | 100 |
| 4 | 500 | 100 |
| 5 | 500 | 100 |
| 6 | 500 | 100 |
| 7 | 500 | 100 |
| 9 | 500 | 100 |
| 10 | 500 | 100 |
| 11 | 500 | 100 |
| 12 | 500 | 100 |
| 13 | 500 | 100 |
| 14 | 500 | 100 |

Test Example 2

Insecticidal Effect on Larvae of Diamond Back Moth (*Plutella xylostella*)

A disc (6 cm in diameter) cut out of a cabbage leaf was soaked for 1 minute in an aqueous suspension of the agricultural and horticultural insecticide of the invention prepared in accordance with Formulation Example 1, air-dried, and placed in a plastic cup (inner diameter: 7 cm). Five 3-instar larvae of *Plutella xylostella* were set free in the cup (duplicates at a concentration). The cup was kept in a constant temperature room at 25° C., and the death and agony of the larvae were examined after 4 days from the treatment to obtain a death rate (%) taking an agonizing insect as a ½ dead insect. The results obtained are shown in Table 3 (the compound numbers in the Table below correspond to the numbers in Table 1).

TABLE 3

| Compound No. | Concentration (ppm) | Death Rate (%) |
|---|---|---|
| 1 | 500 | 100 |
| 2 | 500 | 100 |
| 3 | 500 | 100 |
| 4 | 500 | 100 |
| 5 | 500 | 100 |
| 6 | 500 | 100 |
| 7 | 500 | 100 |
| 9 | 500 | 100 |
| 10 | 500 | 100 |
| 11 | 500 | 100 |
| 12 | 500 | 100 |
| 13 | 500 | 100 |
| 14 | 500 | 100 |
| 15 | 500 | 100 |

Test Example 3

Insecticidal Effect on Larvae of Common Cutworm (*Spodoptera litura*)

A disc (6 cm in diameter) cut out of a cabbage leaf was soaked for 1 minute in an aqueous suspension of an agricultural and horticultural insecticide of the invention prepared in accordance with Formulation Example 1, air-dried, and placed in a plastic cup (inner diameter: 7 cm). Five 3-instar larvae of *Spodoptera litura* were set free in the cup (duplicates at a concentration). The cup was kept in a constant temperature room at 25° C., and the death and agony of the larvae were examined after 5 days from the treatment to obtain a death rate (%) taking an agonizing insect as a ½ dead insect. The results obtained are shown in Table 4 (the compound numbers in the Table below correspond to the numbers in Table 1).

TABLE 4

| Compound No. | Concentration (ppm) | Death Rate (%) |
|---|---|---|
| 5 | 500 | 100 |
| 6 | 500 | 100 |
| 9 | 500 | 100 |
| 11 | 500 | 90 |
| 13 | 500 | 100 |
| 14 | 500 | 100 |
| 15 | 500 | 100 |

Test Example 4

Insecticidal Effect on Imagoes of Adzuki Bean Weevil (*Callosobruchus chinensis*)

Two adzuki beans were put in a glass cylinder (inner diameter: 3 cm×length: 15 cm), and 10 imagoes of *Callosobruchus chinensis* were set free therein. An agricultural and horticultural insecticide of the invention was prepared in accordance with Formulation Example 3 and diluted with water, and 0.3 ml of the resulting emulsion was sprayed in the glass cylinder by means of a spray tower (manufactured by Mizuho Rika) (duplicates at a concentration). The cylinder was kept in a constant temperature room at 25° C., and the mortality and agony of the larvae were examined after 4 days from the treatment to obtain a death rate (%) taking an agonizing insect as a ½ dead insect. The results obtained are shown in Table 5 (the compound numbers in the Table correspond to the numbers in Table 1).

TABLE 5

| Compound No. | Concentration (ppm) | Death Rate (%) |
|---|---|---|
| 1 | 500 | 100 |
| 2 | 500 | 100 |
| 3 | 500 | 100 |
| 4 | 500 | 100 |
| 5 | 500 | 100 |
| 6 | 500 | 100 |
| 9 | 500 | 100 |
| 10 | 500 | 100 |
| 11 | 500 | 100 |
| 12 | 500 | 100 |
| 13 | 500 | 100 |
| 14 | 500 | 100 |
| 15 | 500 | 100 |

Test Example 5

Insecticidal Effect on Larvae of Green Peach Aphid (*Myzus persicae*)

Water was put in a screw bottle (volume: 10 ml), and a leafstalk of Japanese radish was placed therein and inoculated with 5 to 6 imagoes of *Myzus persicae* per leave. After the inoculation, the bottle was put in a glass cylinder (diameter: 0.5 cm; height: 15 cm) with a mesh cover, and the insects were let to proliferate in a constant temperature room kept at 25° C. for 3 days. The imagoes on the leaves were removed, and the leaves were dipped in an aqueous dilusion of an agricultural and horticultural insecticide prepared of the invention in accordance with Formulation Example 3 for about 5 seconds and then returned into the glass cylinder (duplicates at a concentration). The cylinder was kept in the constant temperature room at 25° C., and the number of the insects on the leaves was counted on the 4th day after the treatment to obtain a death rate (%). The results obtained are shown in Table 6 (the compound numbers in the Table correspond to the numbers in Table 1).

TABLE 6

| Compound No. | Concentration (ppm) | Death Rate (%) |
|---|---|---|
| 1 | 500 | 100 |
| 2 | 500 | 100 |
| 3 | 500 | 100 |
| 4 | 500 | 100 |
| 5 | 500 | 100 |
| 7 | 500 | 100 |
| 8 | 500 | 100 |
| 9 | 500 | 100 |
| 10 | 500 | 100 |
| 12 | 500 | 100 |
| 13 | 500 | 100 |
| 14 | 500 | 100 |

Test Example 6

Insecticidal Effect on Larvae of Brown Rice Planthopper (*Nilaparvata lugens*)

Roots of young rice seedlings (height: about 10 cm) planted in a plastic cup were washed with water and soil was washed away so as not to damage the fine roots. The stem was pinched by a urethane tip (diameter: 3 cm, height: 2 cm) having a cut line and the roots were inserted into an Erlenmeyer flask to which 50 ml of an agent solution (an aqueous diluted solution of agricultural and horticultural insecticide of the invention prepared in accordance with Formulation Example 1) was placed beforehand (2 to 3 young rice seedlings/flask). The urethane tip was wedged into the mouse of the flask to fix the rice seedlings. A glass tube (diameter: 3 cm, height: 5 cm) was placed thereon, wedged into the urethane tip, and fixed with a tape. The flask in such state was kept in a constant temperature room at 25° C. for 3 days. Five larvae of brown rice planthopper were placed in the glass tube and then the tube was capped with a urethane tip, followed by keeping in the constant temperature room at 25° C. (duplicates at a concentration). The mortality and agony of the larvae were examined on 4th day after the treatment to obtain a death rate (%) taking an agonizing insect as a ½ dead insect. This test was carried out on three agent solutions different in the concentration of the active ingredient. The results are shown in Table 7 (the compound numbers in the table correspond to the numbers in Table 1).

As comparative compounds I to V, each compound having a structure shown below (Compound I described in Japanese Patent Laid-Open No. 316771/1988, Compounds II and III described in Examples of WO9845274, and Compounds IV and V included in the claim of WO9845274 but not included in the claim of the present application) was similarly subjected to the test.

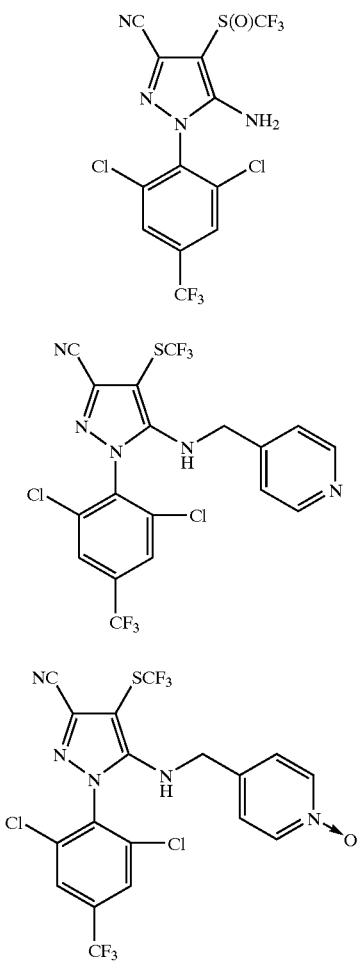

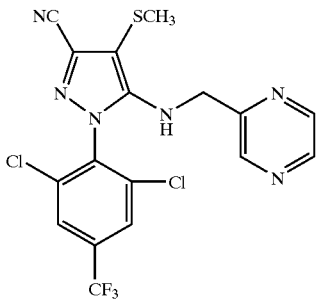

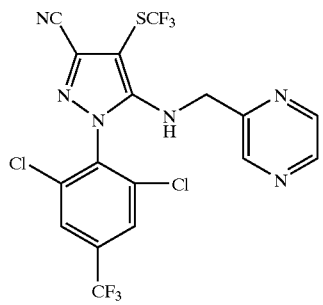

TABLE 7

| Death Rate (%) at Each Concentration of Active Ingrediet | | | |
|---|---|---|---|
| | 3.1 ppm | 0.8 ppm | 0.2 ppm |
| Compound No. | | | |
| 1 | 100 | 100 | 100 |
| 3 | 100 | 100 | 100 |
| 4 | 100 | 100 | 100 |
| 5 | 100 | 100 | 100 |
| 7 | 100 | 100 | 100 |
| 8 | 100 | 100 | 100 |
| 9 | 100 | 100 | 100 |
| 10 | 100 | 100 | 100 |
| 14 | 100 | 100 | 100 |
| (Comparative Compounds) | | | |
| I | 92 | 67 | 33 |
| II | 50 | 20 | — |
| III | 100 | 100 | 92 |
| IV | 100 | 100 | 100 |
| V | 95 | 80 | 55 |

Brown rice planthopper (*Nilaparvata lugens*) is a highly problematic pest insect species which is harmful as described in Test Example 1, but a sufficient effect can not be attained by the application method of spraying an agent to stems and leafs, provided that the detection is delayed or that an enough amount of the agent is not spread to the roots.

Since this insect species has a characteristic of making its habitat around the roots of rice plant or the like and harming the plant through sucking fluid, more efficient method of controlling the insect may be a method of treating the surface of soil with an agent (granule treatment) before the outbreak of the species occurs widely. However, in order to attain a high controlling effect, a systemic property (a penetrating and migrating property) into a plant body is required as the nature of the agent. As apparent from Table 6, all of the compounds of the invention and Compounds III and IV exhibited an insecticidal activity through a high systemic property against this species of highly problematic pest insect, but Compounds I, II, and III had an obviously inferior effect as compared with the compounds of the invention owing to their low such action.

Test Example 7

Test on Toxicity to Fish Using *Oryzias latipes*

This test example is one example for examining safety of agricultural and horticultural insecticides to the environment.

Ten mg of each compound was dissolved in 1 ml of dimethyl sulfoxide and a 0.05 ml portion thereof was added to a glass beaker containing 1 liter of distilled water to obtain a 0.5 ppm aqueous solution. Into the aqueous solution was put five fishes of *Oryzias latipes* (adult, average weight: about 360 mg) and the mortality was examined after 48 hours to calculate a death rate (%) (5 fishes per 1 lot/beaker, single run). The results are shown in Table 8 (the compound numbers in the table correspond to the numbers in Table 1).

Similar to Test Example 6, Compound I described in Japanese Patent Laid-Open No. 316771/1988, Compounds II and III described in Examples of WO9845274, and Compounds IV and V included in the claim of WO9845274 but not included in the claim of the present application were subjected to the test, as comparative compounds.

TABLE 8

| Compound No. | Toxicity to fish (%) |
|---|---|
| 1 | 0 |
| 2 | 0 |
| 8 | 0 |
| 9 | 0 |
| 10 | 0 |
| 13 | 0 |
| 14 | 0 |
| 15 | 0 |
| (Comparative Compounds) | |
| I | 100 |
| II | 80 |
| III | 60 |
| IV | 100 |
| V | 100 |

As apparent from Table 8, all the tests on Compounds I to V showed a high death rate of the fish, but no death was observed in the case of the compounds of the invention. Thus, the compounds of the invention are well employable even when a control agent is directly applied to water system, for example, the case of paddy rice.

Test Example 8

Insecticidal Effect on Cat Flea

Onto a round filter (diameter: 10 cm) was added dropwise 0.7 ml of an agent solution diluted to a predetermined concentration. After drying, the filter was placed on the bottom of a cylinder (diameter: 10 cm×height: 30 cm). Ten fleas were set free therein and the mortality was examined on 1st day and 2nd day after the treatment to calculate a death rate (%) based on the results. The results are shown in Table 9 (the compound numbers in the table correspond to the numbers in Table 1).

TABLE 9

| Compound No. | Amount of Agent Tested (mg/filter) | Death Rate (%) |
|---|---|---|
| 5 | 0.7 | 100 |
| 7 | 0.7 | 100 |

INDUSTRIAL APPLICABILITY

The 1-aryl-3-cyano-5-pyrazinylalkylaminopyrazole derivatives of the invention are novel compounds having excellent insecticidal effects and broad insecticidal spectra, and also exhibiting a high systemic activity and reduced toxicity to the environment such as toxicity to fishes. Thus, the derivatives are useful as pest control agents.

What is claimed is:

1. A 1-aryl-3-cyano-5-heteroarylalkylaminopyrazole derivative represented by formula (1):

wherein group A is (A-1):

X represents N or C-halogen; $R^1$ represents alkyl, alkenyl, alkynyl or haloalkyl; $R^2$ represents hydrogen, alkyl or linear or branched alkylcarbonyl; $R^3$ represents hydrogen or alkyl; $R^4$ represents hydrogen, alkyl or halogen; and n represents 0, 1 or 2, with the proviso that $R^1$ is not perhaloalkyl when n is 0.

2. The 1-aryl-3-cyano-5-heteroarylalkylaminopyrazole derivative according to claim 1, wherein $R^4$ is hydrogen or alkyl.

3. The 1-aryl-3-cyano-5-heteroarylalkylaminopyrazole derivative according to claim 1, wherein $R^1$ is $C_{1-4}$-alkyl or $C_{1-4}$-haloalkyl.

4. The 1-aryl-3-cyano-5-heteroarylalkylaminopyrazole derivative according to claim 3, wherein $R^1$ is $C_{1-2}$-haloalkyl.

5. 1-(2,6-Dichloro-4-trifluoromethylphenyl)-4-fluoromethylthio-5-(pyrazin-2-ylmethylamino)pyrazole-3-carbonitrile and 1-(2,6-dichloro-4-trifluoromethylphenyl)-4-trifluoromethylsulfinyl-5-(pyrazin-2-ylmethylamino) pyrazol-3-carbonitrile.

6. A pest control composition, comprising:

the 1-aryl-3-cyano-5-heteroarylalkylaminopyrazole derivative according to claim 1 with a carrier and optionally at least one auxiliary.

7. A pyrazole derivative represented by formula (2):

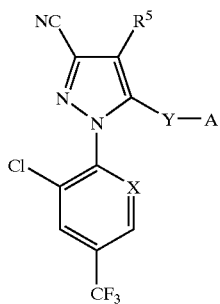

(2)

wherein group A is (A-1):

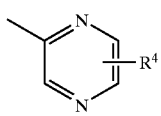

wherein bridging group Y is

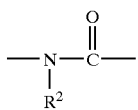  Y-1

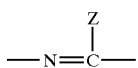  Y-2 or

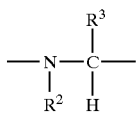  Y-3 and wherein X represents N or C-halogen; $R^2$ represents hydrogen, alkyl or linear or branched alkylcarbonyl; $R^3$ represents hydrogen or alkyl and $R^4$ represents hydrogen, alkyl or halogen; and $R^5$ represents hydrogen, thiocyanato, dithio which links two pyrazole rings or mercapto and Z represents halogen.

8. A process for producing a pyrazole derivative of formula (1)

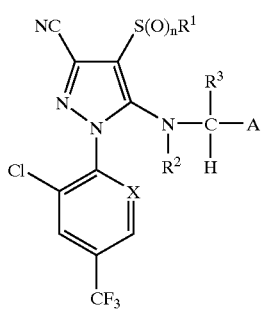

(1)

wherein group A is (A-1):

X represents N or C-halogen; $R^1$ represents alkyl, alkenyl, alkynyl or haloalkyl; $R^2$ represents hydrogen, alkyl or linear or branched alkylcarbonyl; $R^3$ represents hydrogen or alkyl; $R^4$ represents hydrogen, alkyl or halogen; and n represents 0, 1 or 2, with the proviso that $R^1$ is not perhaloalkyl when n is 0, which comprises:

treating a pyrazole derivative of formula (2):

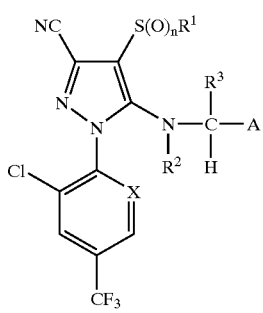

(2)

wherein A is as defined above, $R^5$ is hydrogen and Y is Y-3:

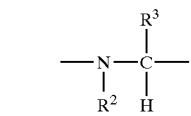

with $R^1S(O)_nX^1$, wherein $R^1$ has the same meaning as defined above, n is 0 or 1 and X is chlorine or bromine.

9. A process for producing a pyrazole derivative of formula (1)

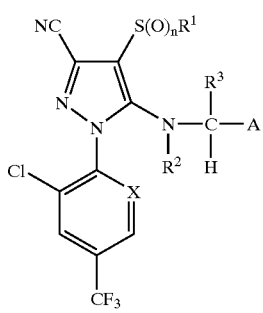

(1)

wherein group A is (A-1):

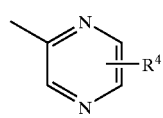

X represents N or C-halogen; $R^1$ represents alkyl, alkenyl, alkynyl or haloalkyl; $R^2$ represents hydrogen, alkyl or linear or branched alkylcarbonyl; $R^3$ represents hydrogen or alkyl; $R^4$ represents hydrogen, alkyl or halogen; and n represents 1 or 2, which comprises:

oxidizing the exocyclic sulfur atom on the pyrazole ring of the compound of formula (1) when n is 0.

10. A process for producing a pyrazole derivative of formula (1)

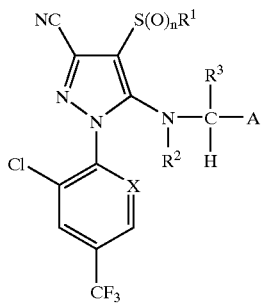

wherein group A is (A-1):

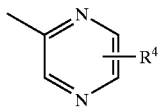

X represents N or C-halogen; $R^1$ represents alkyl, alkenyl, alkynyl or haloalkyl; $R^2$ represents hydrogen, alkyl or linear or branched alkylcarbonyl; $R^3$ represents hydrogen or alkyl; $R^4$ represents hydrogen, alkyl or halogen; and n represents 0, with the proviso that $R^1$ is not perhaloalkyl, which comprises:

treating a pyrazole derivative of formula (2):

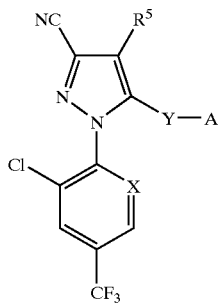

wherein A is as defined above, $R^5$ is thiocyanato and Y is Y-3:

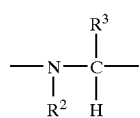

with $R^1$-$X^2$, wherein $R^1$ has the same meaning as defined above and $X^2$ represents halogen or trimethylsilyl.

11. A process for producing a pyrazole derivative of formula (1)

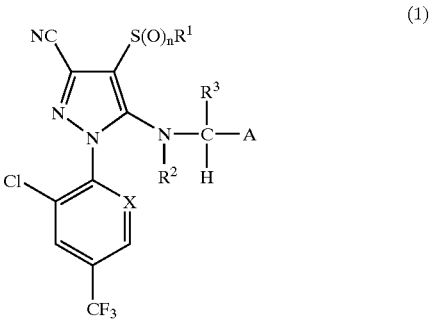

wherein group A is (A-1):

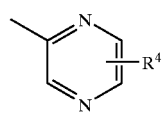

X represents N or C-halogen; $R^1$ represents alkyl, alkenyl, alkynyl or haloalkyl; $R^2$ represents hydrogen, alkyl or linear or branched alkylcarbonyl; $R^3$ represents hydrogen or alkyl; $R^4$ represents hydrogen, alkyl or halogen; and n represents 0, with the proviso that $R^1$ is not perhaloalkyl, which comprises:

treating a pyrazole derivative of formula (2):

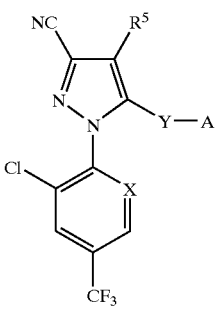

wherein A is as defined above, $R^5$ is mercapto and Y is Y-3:

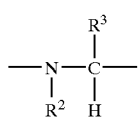

with $R^1$-$X^3$, wherein $R^1$ has the same meaning as defined above and $X^3$ represents halogen.

12. A process for producing a pyrazole derivative of formula (1)

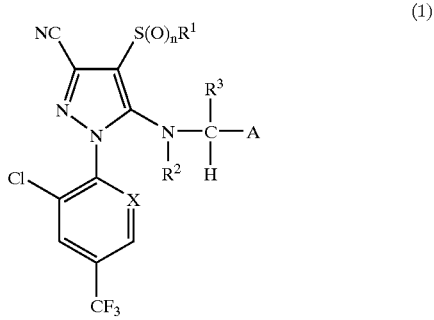

wherein group A is (A-1):

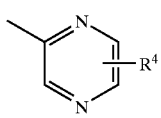

X represents N or C-halogen; $R^1$ represents alkyl, alkenyl, alkynyl or haloalkyl; $R^2$ represents hydrogen, alkyl or linear or branched alkylcarbonyl; $R^3$ represents hydrogen; $R^4$ represents hydrogen, alkyl or halogen; and n represents 0, with the proviso that $R^1$ is not perhaloalkyl, which comprises:

treating a pyrazole derivative of formula (2):

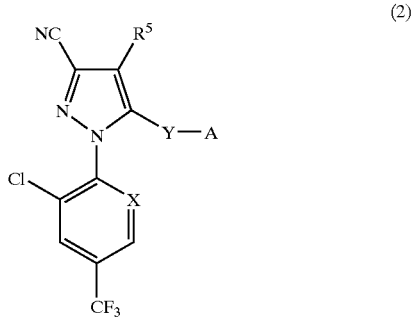

wherein A is as defined above, $R^5$ is dithio which links two pyrazole rings and

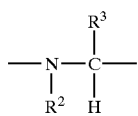

Y is Y-3:

with $R^1$-$X^4$, wherein $R^1$ has the same meaning as defined above and $X^4$ represents halogen or $SO_2M$, wherein M is an alkali metal.

13. A process for producing a pyrazole derivative of formula (1)

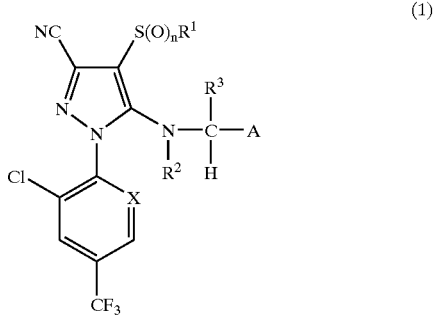

wherein group A is (A-1):

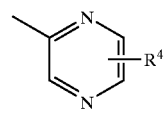

X represents N or C-halogen; $R^1$ represents alkyl, alkenyl, alkynyl or haloalkyl each of which bears at least one fluorine atom; $R^2$ represents hydrogen, alkyl or linear or branched alkylcarbonyl; $R^3$ represents hydrogen or alkyl; $R^4$ represents hydrogen, alkyl or halogen; and n represents 0, 1 or 2, with the proviso that $R^1$ is not perhaloalkyl when n is 0, which comprises:

treating a pyrazole derivative of formula (1):

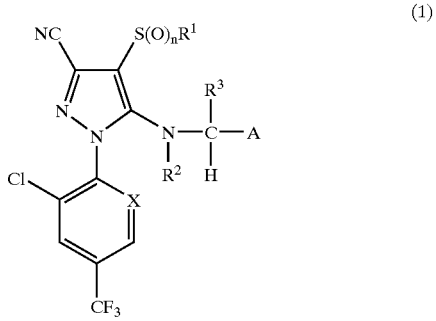

wherein A is as defined above, and $R^1$ is an alkyl group having at least one chlorine atom or bromine atom, with a fluorinating agent selected from the group consisting of hydrogen fluoride, a mixture of hydrogen fluoride and an amine, and a metal fluoride.

14. The process of producing the pyrazole derivative of claim 8, wherein $R^1$ is haloalkyl of 1 or 2 carbon atoms.

15. The process of producing the pyrazole derivative of claim 9, wherein $R^1$ is haloalkyl of 1 or 2 carbon atoms.

16. The process of producing the pyrazole derivative of claim 10, wherein $R^1$ is haloalkyl of 1 or 2 carbon atoms.

17. The process of producing the pyrazole derivative of claim 11, wherein $R^1$ is haloalkyl of 1 or 2 carbon atoms.

18. The process of producing the pyrazole derivative of claim 12, wherein $R^1$ is haloalkyl of 1 or 2 carbon atoms.

19. The process of producing the pyrazole derivative of claim 13, wherein $R^1$ is haloalkyl of 1 or 2 carbon atoms.

20. A process for producing a pyrazole derivative of formula (2):

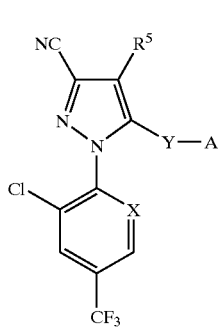

(2)

wherein Y is Y-3:

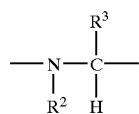

wherein $R^2$ is hydrogen, $R^3$ is hydrogen or alkyl and $R^5$ is hydrogen, thiocyanato, a dithio group which links two pyrazole rings or mercapto, which comprises:

treating a pyrazole derivative of formula (3):

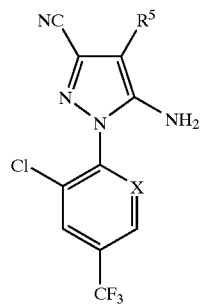

(3)

wherein X represents N or C-halogen, with a nitrogen-containing six-membered heterocyclic compound of the formula: A—CH(—$R^3$)—$X^5$, $X^5$ of which is halogen, lower alkylsulfonyloxy or arylsulfonyloxy wherein A is (A-1):

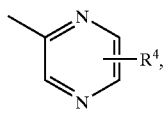

$R^4$ of which is hydrogen, alkyl or halogen.

21. A process for producing a pyrazole derivative of formula (2):

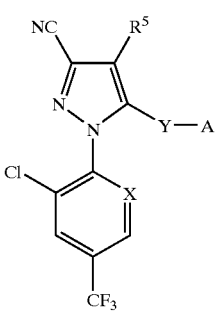

(2)

wherein Y is Y-3:

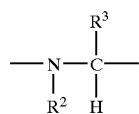

wherein $R^2$ is hydrogen and $R^3$ is hydrogen or alkyl, which comprises:

treating a pyrazole derivative of formula (4):

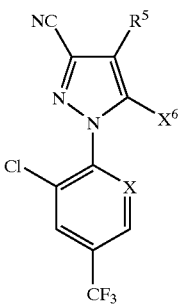

(4)

wherein X represents N or C-halogen; $R^5$ represents hydrogen, thiocyanato, dithio which links two pyrazole rings or mercapto and $X^6$ represents halogen, lower alkylsulfonyloxy or arylsulfonyloxy with a nitrogen-containing six-membered heterocyclic compound of the formula: A—CH(—$R^3$)—$NH_2$, wherein $R^3$ is as defined above, wherein A is (A-1):

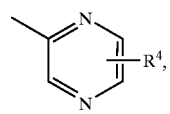

wherein $R^4$ is hydrogen, alkyl or halogen.

22. A process for producing a pyrazole derivative of formula (2):

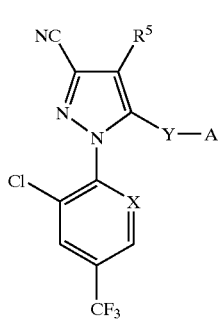 (2)

wherein Y is Y-1:

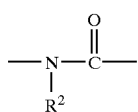

wherein $R^2$ is hydrogen, X is N or C-halogen, and $R^5$ is hydrogen, thiocyanato, a dithio group which links two pyrazole rings or mercapto, which comprises:

treating a pyrazole derivative of formula (3):

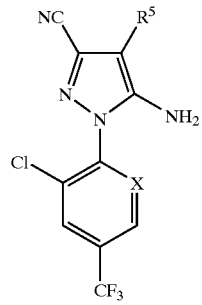 (3)

with a nitrogen-containing six-membered heterocyclic compound of the formula: $A—C(=O)—X^7$, wherein $X^7$ is hydroxyl, $C_{1-6}$-alkoxy or halogen, wherein A is (A-1):

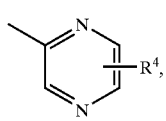

$R^4$ of which is hydrogen, alkyl or halogen.

23. A process for producing a pyrazole derivative of formula (2):

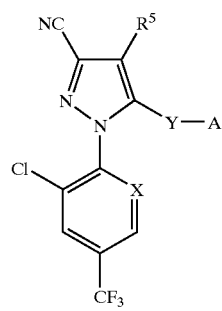 (2)

wherein A is

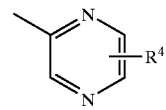

and Y is Y-2:

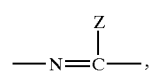

wherein Z is chlorine or which comprises:

treating an amide of formula (2):

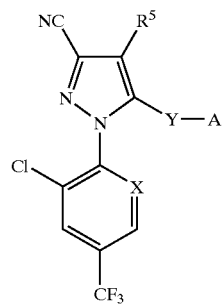 (2)

wherein Y is (Y-1):

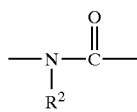

and $R^2$ represents hydrogen, with phosphorus pentachloride, phosphorus pentabromide, phosphorus oxychloride, phosphorus oxybromide, thionyl chloride or thionyl bromide.

24. A process for producing a pyrazole derivative of formula (2):

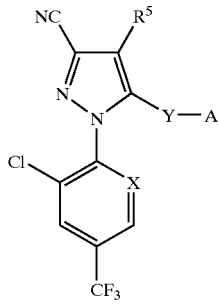

(2)

wherein $R^5$ is hydrogen, thiocyanato, a dithio group which links two pyrazole rings or mercapto, A is

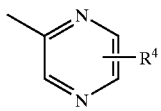

and Y is Y-3:

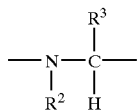

wherein $R^2$ is hydrogen, alkyl or linear or branched alkylcarbonyl and $R^3$ is hydrogen, which comprises:

reducing an amide compound or a haloimidate compound represented by formula (2), wherein Y is Y-1 or Y-2

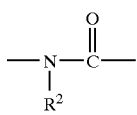
Y-1

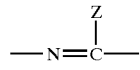
Y-2 wherein $R^3$ is as defined above and Z is chlorine or bromine.

25. The 1-aryl-3-cyano-5-heteroarylalkylaminopyrazole derivative according to claim 1, wherein said linear or branched alkylcarbonyl is linear or branched $C_{1-4}$-alkylcarbonyl.

26. The 1-aryl-3-cyano-5-heteroarylalkylaminopyrazole derivative according to claim 7, wherein said linear or branched alkylcarbonyl is linear or branched $C_{1-4}$-alkylcarbonyl.

27. The 1-aryl-3-cyano-5-heteroarylalkylaminopyrazole derivative according to claim 8, wherein said linear or branched alkylcarbonyl is linear or branched $C_{1-4}$-alkylcarbonyl.

28. The 1-aryl-3-cyano-5-heteroarylalkylaminopyrazole derivative according to claim 9, wherein said linear or branched alkylcarbonyl is linear or branched $C_{1-4}$-alkylcarbonyl.

29. The 1-aryl-3-cyano-5-heteroarylalkylaminopyrazole derivative according to claim 11, wherein said linear or branched alkylcarbonyl is linear or branched $C_{1-4}$-alkylcarbonyl.

30. The 1-aryl-3-cyano-5-heteroarylalkylaminopyrazole derivative according to claim 12, wherein said linear or branched alkylcarbonyl is linear or branched $C_{1-4}$-alkylcarbonyl.

31. The 1-aryl-3-cyano-5-heteroarylalkylaminopyrazole derivative according to claim 13, wherein said linear or branched alkylcarbonyl is linear or branched $C_{1-4}$-alkylcarbonyl.

32. The 1-aryl-3-cyano-5-heteroarylalkylaminopyrazole derivative according to claim 12, wherein said linear or branched alkylcarbonyl is linear or branched $C_{1-4}$-alkylcarbonyl.

* * * * *